US011883553B2

(12) United States Patent
Mithani et al.

(10) Patent No.: US 11,883,553 B2
(45) Date of Patent: *Jan. 30, 2024

(54) SEAL INTEGRITY INDICATOR FOR A STERILIZATION CONTAINER

(71) Applicant: O&M Halyard, Inc., Mechanicsville, VA (US)

(72) Inventors: Namita A. Mithani, Alpharetta, GA (US); Anthony Stephen Spencer, Woodstock, GA (US); Tracy J. White, Cumming, GA (US); Edward B. Madsen, Cumming, GA (US); Marshall R. Dean, Cumming, GA (US)

(73) Assignee: O&M Halyard, Inc., Mechanicsville, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/964,313

(22) Filed: Oct. 12, 2022

(65) Prior Publication Data

US 2023/0037088 A1 Feb. 2, 2023

Related U.S. Application Data

(63) Continuation of application No. 16/677,748, filed on Nov. 8, 2019, now Pat. No. 11,511,010.

(Continued)

(51) Int. Cl.
*A61L 2/26* (2006.01)
*A61L 2/07* (2006.01)
(Continued)

(52) U.S. Cl.
CPC ..................... *A61L 2/26* (2013.01);
*A61L 2/07* (2013.01); *A61L 2/14* (2013.01);
*A61L 2/206* (2013.01);
(Continued)

(58) Field of Classification Search
CPC ..... A61L 2/04; A61L 2/07; A61L 2/14; A61L 2/20; A61L 2/206; A61L 2/208;
(Continued)

(56) References Cited

U.S. PATENT DOCUMENTS 4,041,203 A 8/1977 Brock et al.
4,349,118 A 9/1982 Sanderson et al.
(Continued)

FOREIGN PATENT DOCUMENTS

WO WO 99/409424 A1 8/1999
WO WO 01/70581 A2 9/2001
WO WO 2016/032853 A1 3/2016

OTHER PUBLICATIONS

Related U.S. Patent Applications Form.

*Primary Examiner* — Timothy C Cleveland
(74) *Attorney, Agent, or Firm* — Dority & Manning, P.A.

(57) ABSTRACT

Seal integrity indicators for sterilization containers are provided. For example, a seal indicator may indicate whether the container is sufficiently sealed to prevent an ingress of contaminants into the container. If the container is sufficiently sealed, the seal indicator is visible, but if not, the seal indicator is not visible. Thus, the seal indicator undergoes a change in state when the sterilization container transitions from unsealed to sealed, or vice versa, such that a user may ascertain whether the container is properly sealed to maintain the container's sterility. An exemplary seal indicator includes an invertible projection formed with the container gasket that is not visible from outside the container until inverted, due to force applied by the lid, to extend through an opening in the container body. Closure mechanisms for sterilization containers also are provided.

16 Claims, 15 Drawing Sheets

Related U.S. Application Data

(60) Provisional application No. 62/757,870, filed on Nov. 9, 2018.

(51) Int. Cl.
  *A61L 2/14* (2006.01)
  *A61L 2/20* (2006.01)
  *B65D 25/28* (2006.01)
  *B65D 43/02* (2006.01)
  *B65D 51/16* (2006.01)
  *B65D 51/24* (2006.01)

(52) U.S. Cl.
  CPC ..... *B65D 25/2841* (2013.01); *B65D 43/0204* (2013.01); *B65D 51/1616* (2013.01); *B65D 51/242* (2013.01); *A61L 2202/182* (2013.01); *A61L 2202/24* (2013.01)

(58) Field of Classification Search
  CPC .. A61L 2/26; A61L 2202/182; A61L 2202/24; B65D 25/2841; B65D 43/0204; A65D 51/1616; A65D 51/242
  See application file for complete search history.

(56) References Cited

U.S. PATENT DOCUMENTS

| | | |
|---|---|---|
| 4,562,047 A | 12/1985 | Sestal et al. |
| 4,783,321 A | 11/1988 | Spence |
| 6,350,418 B1 | 2/2002 | Venderpool et al. |
| 11,511,010 B2 * | 11/2022 | Mithani ............... A61L 2/26 |
| 2004/0040961 A1 | 3/2004 | Vilata et al. |
| 2013/0280134 A1 | 10/2013 | Hoffman et al. |

* cited by examiner

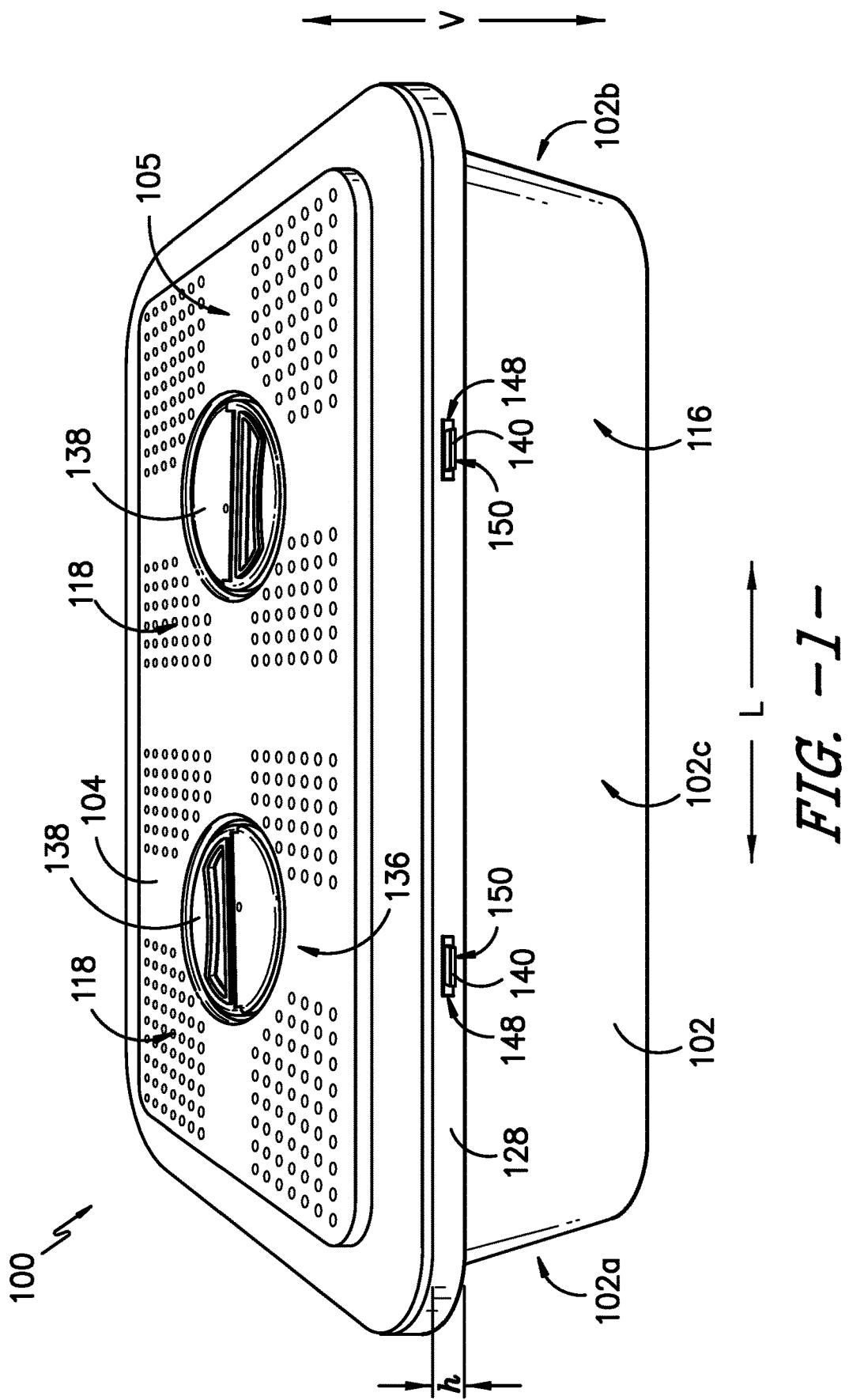
FIG. -1-

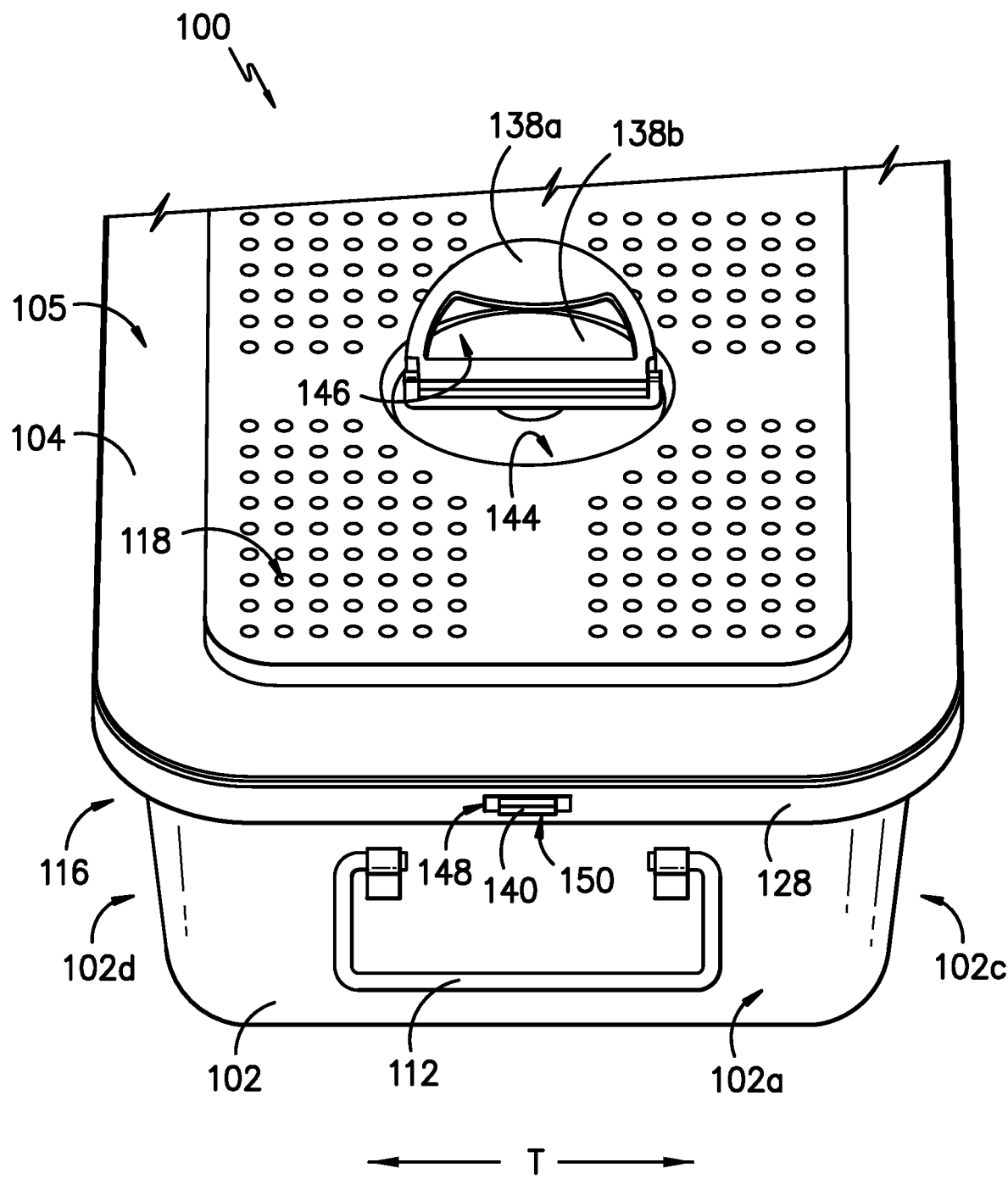
FIG. -2-

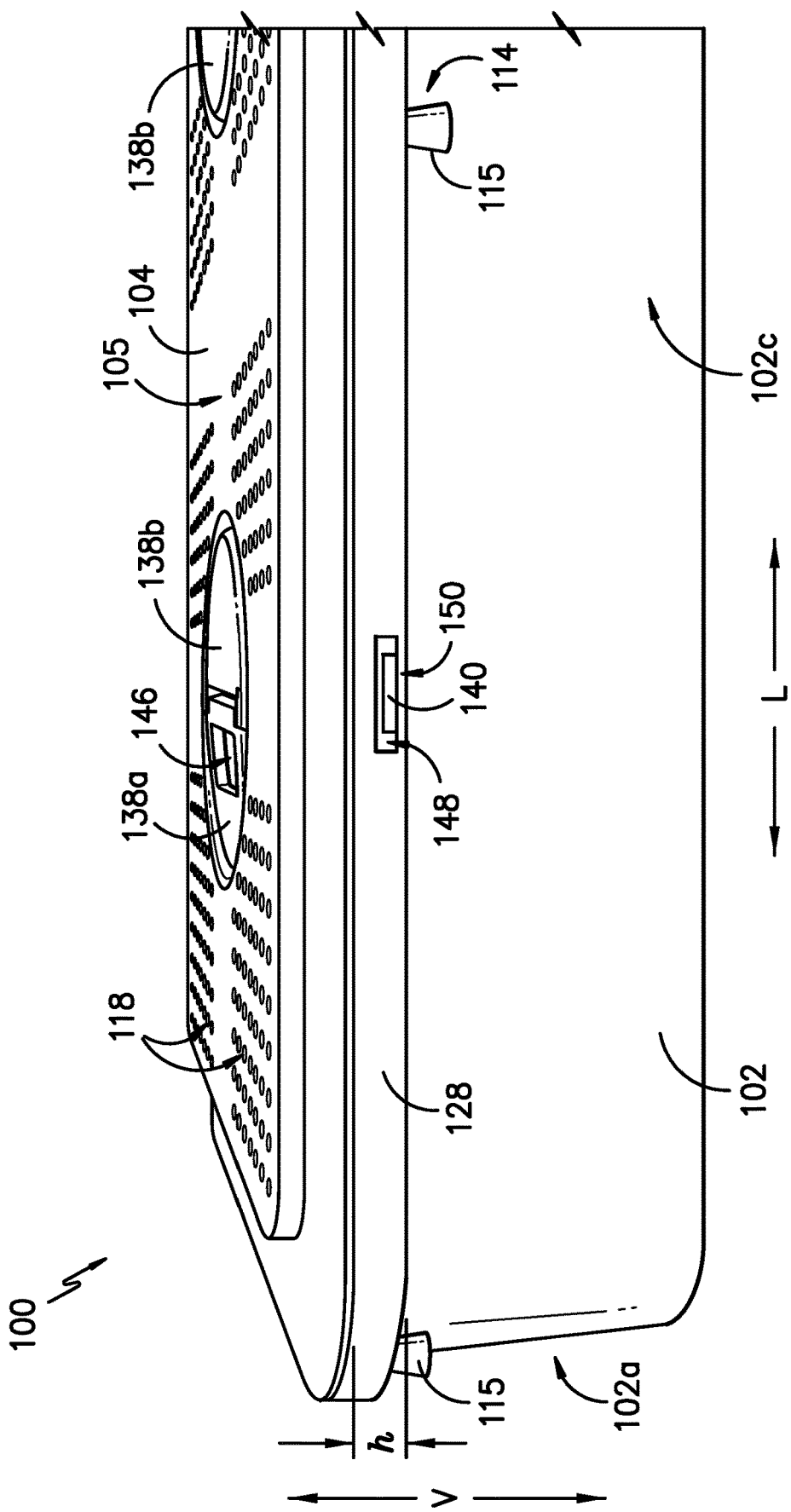
FIG. -3-

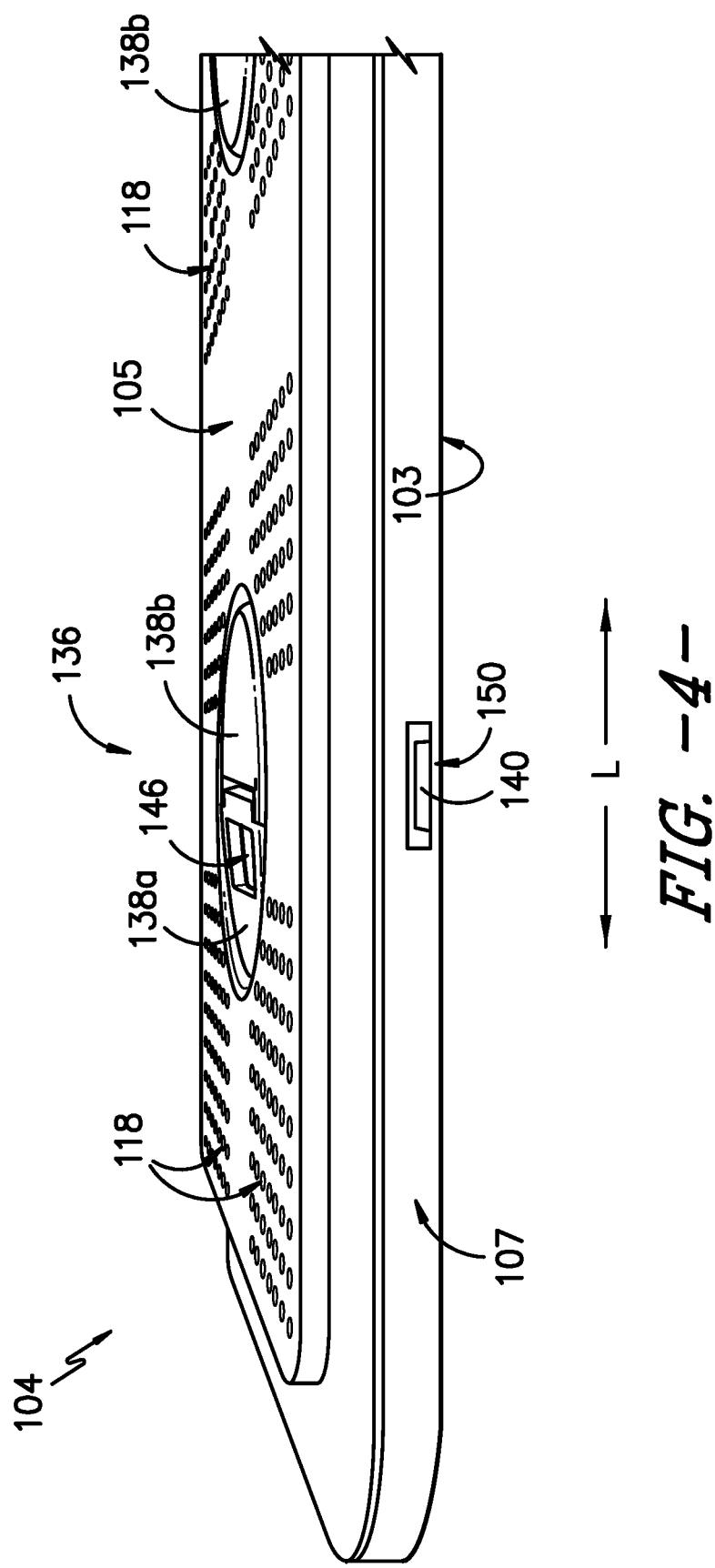
FIG. -4-

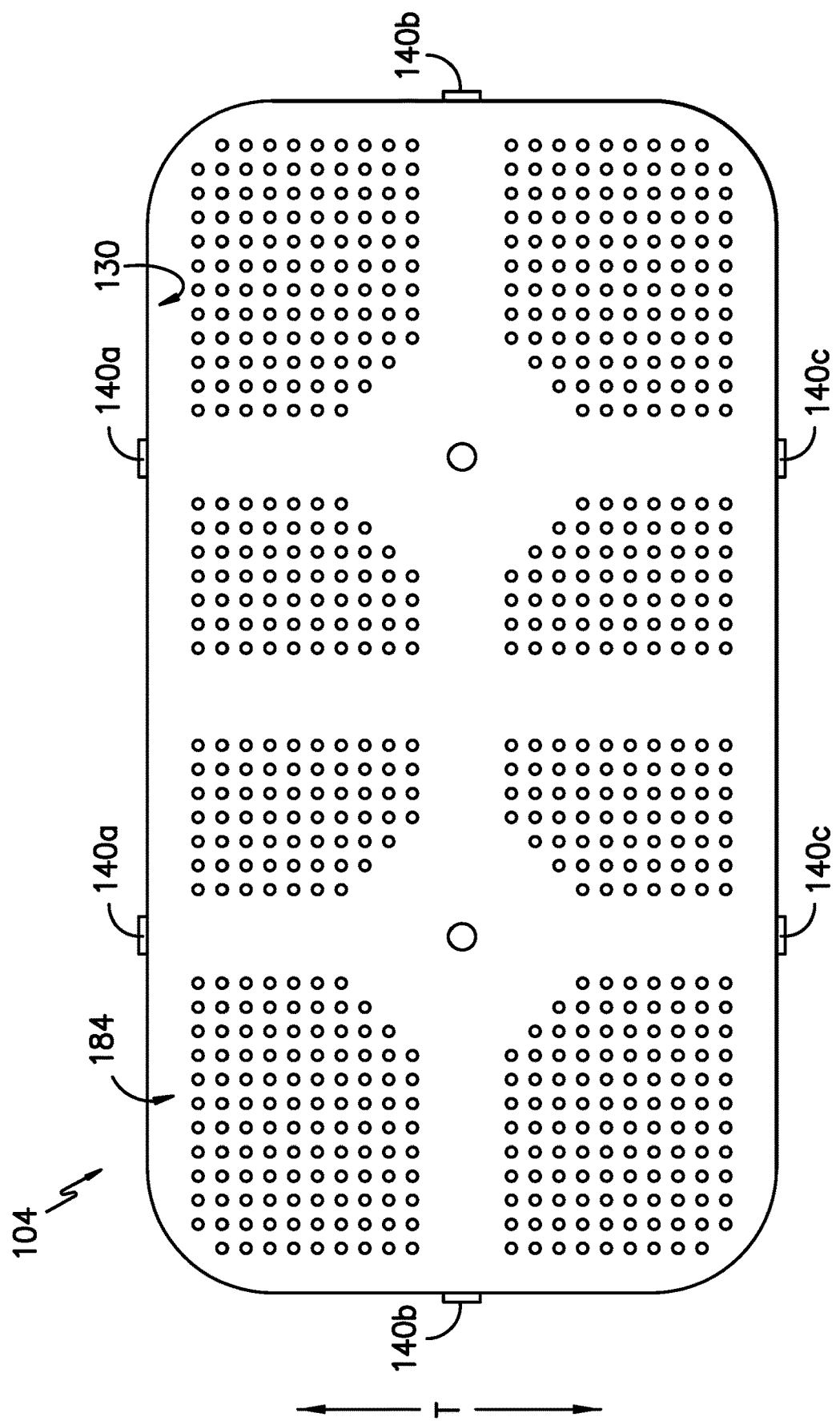
FIG. -5-

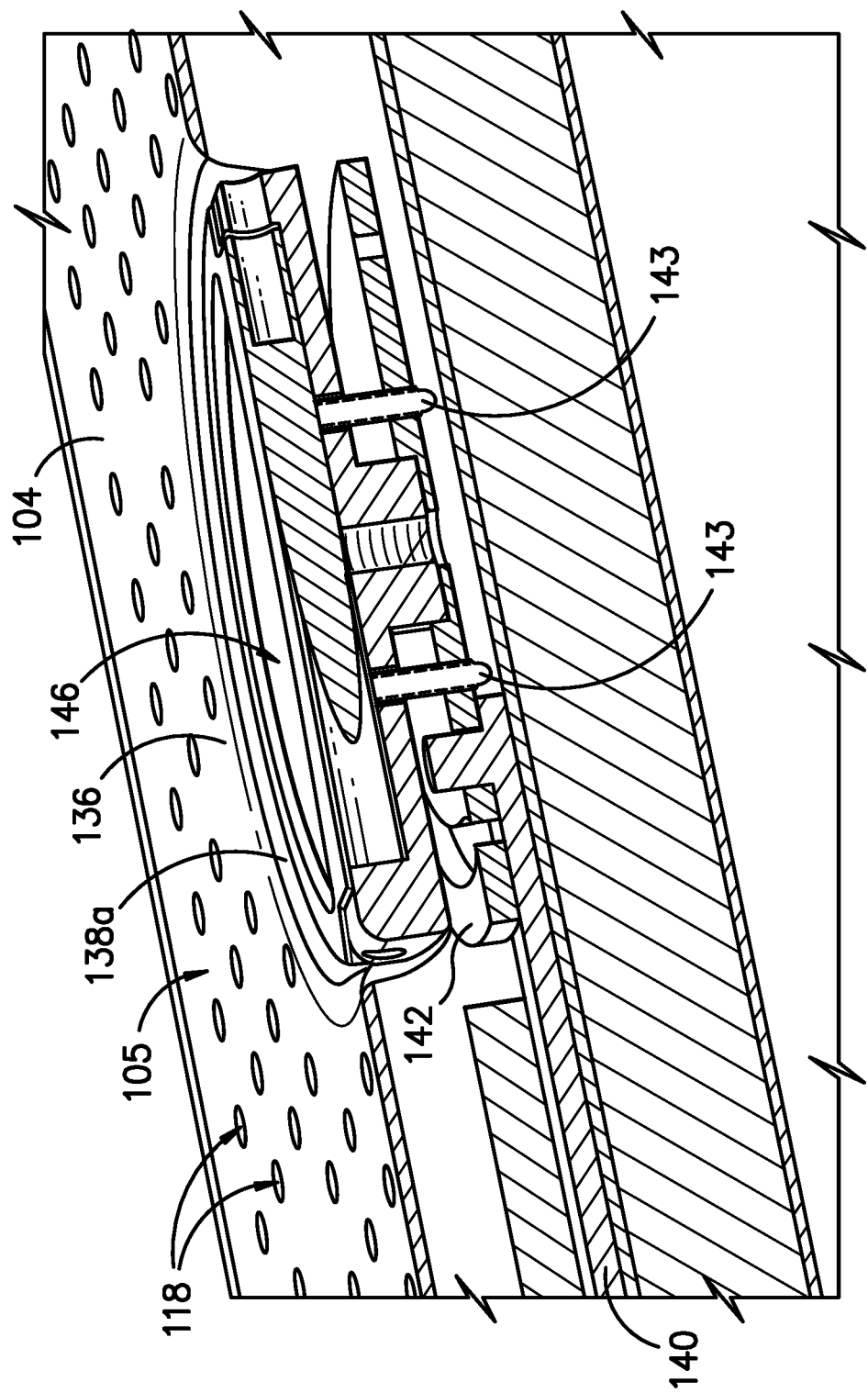
FIG. -6-

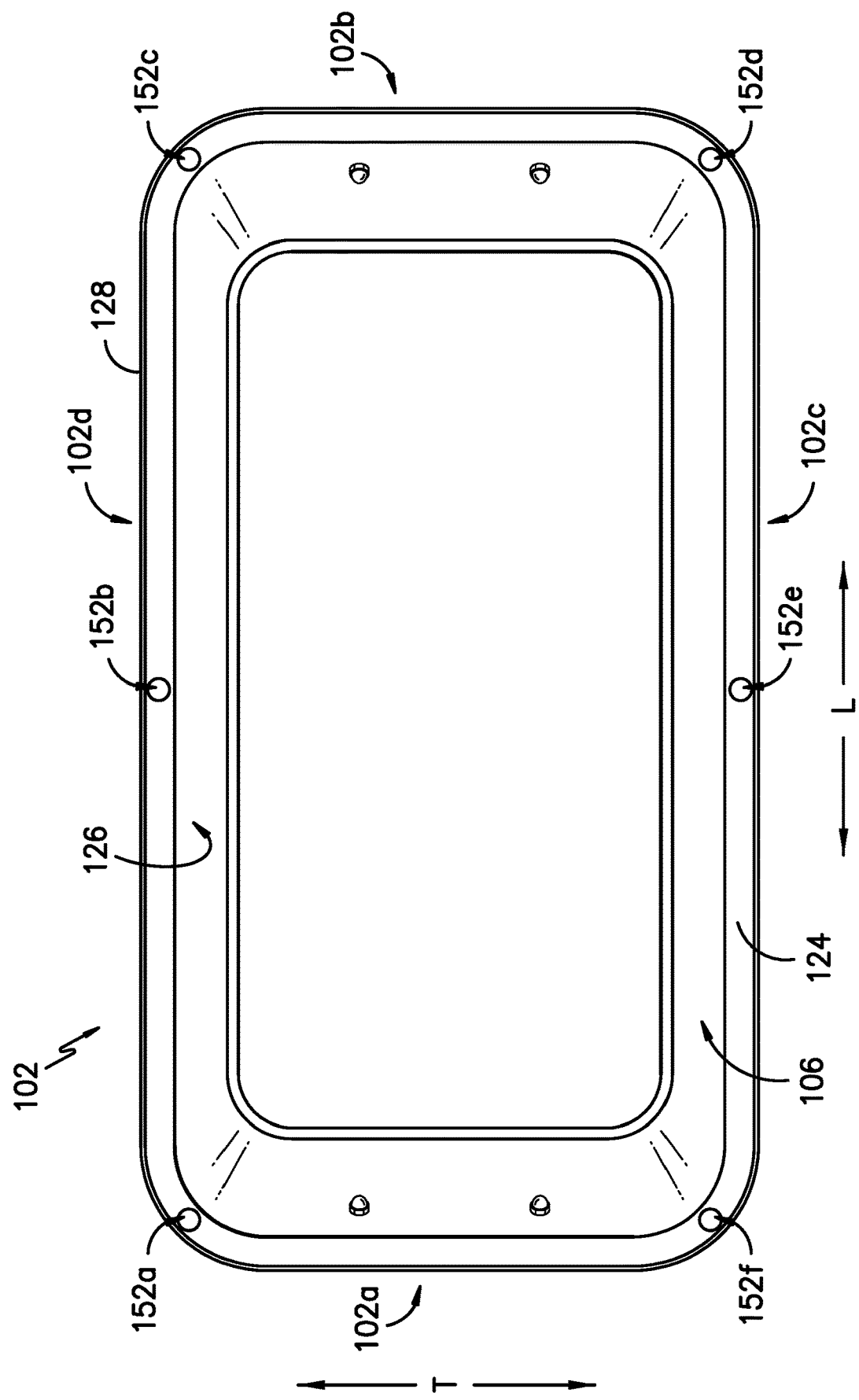

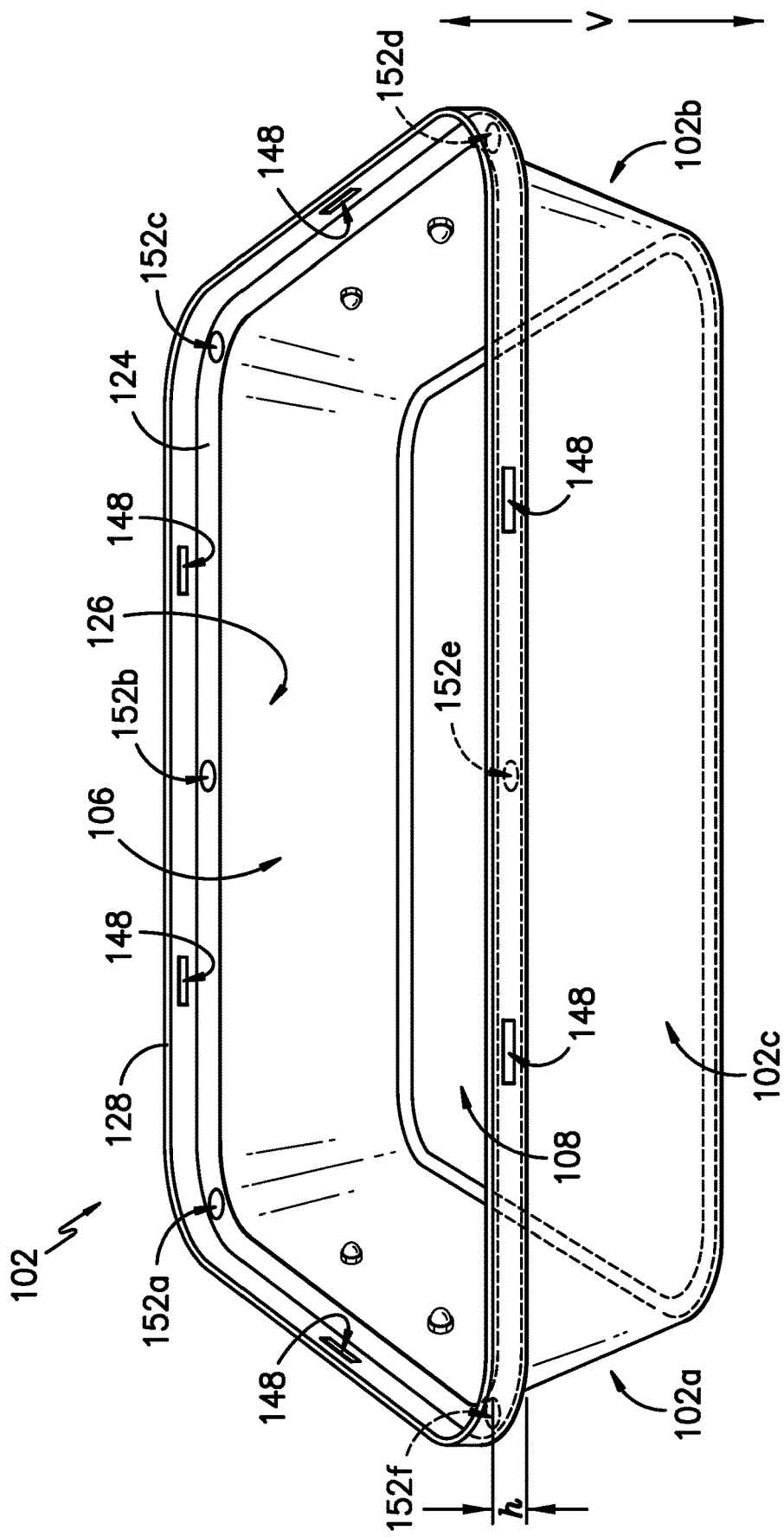
FIG. -8-

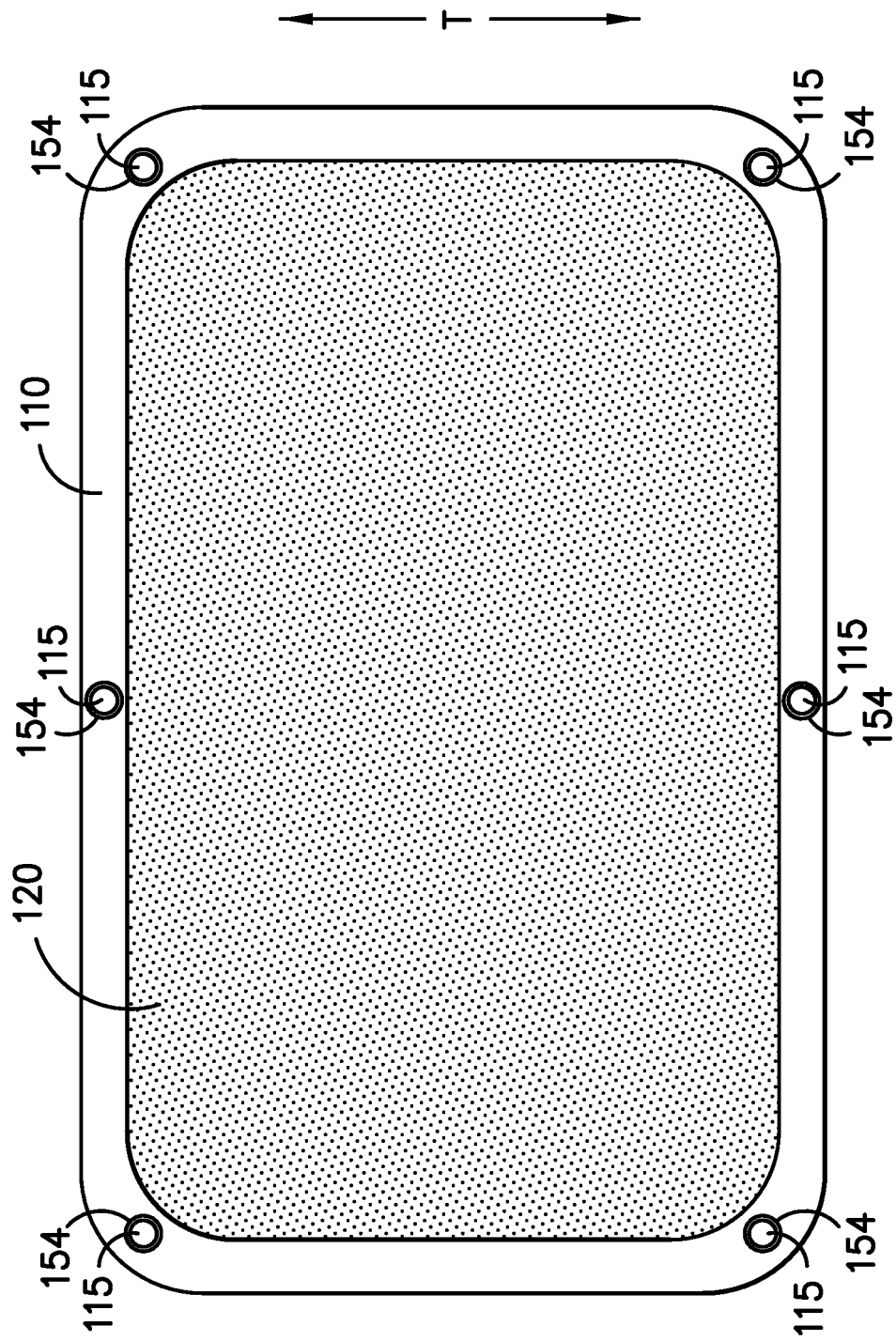

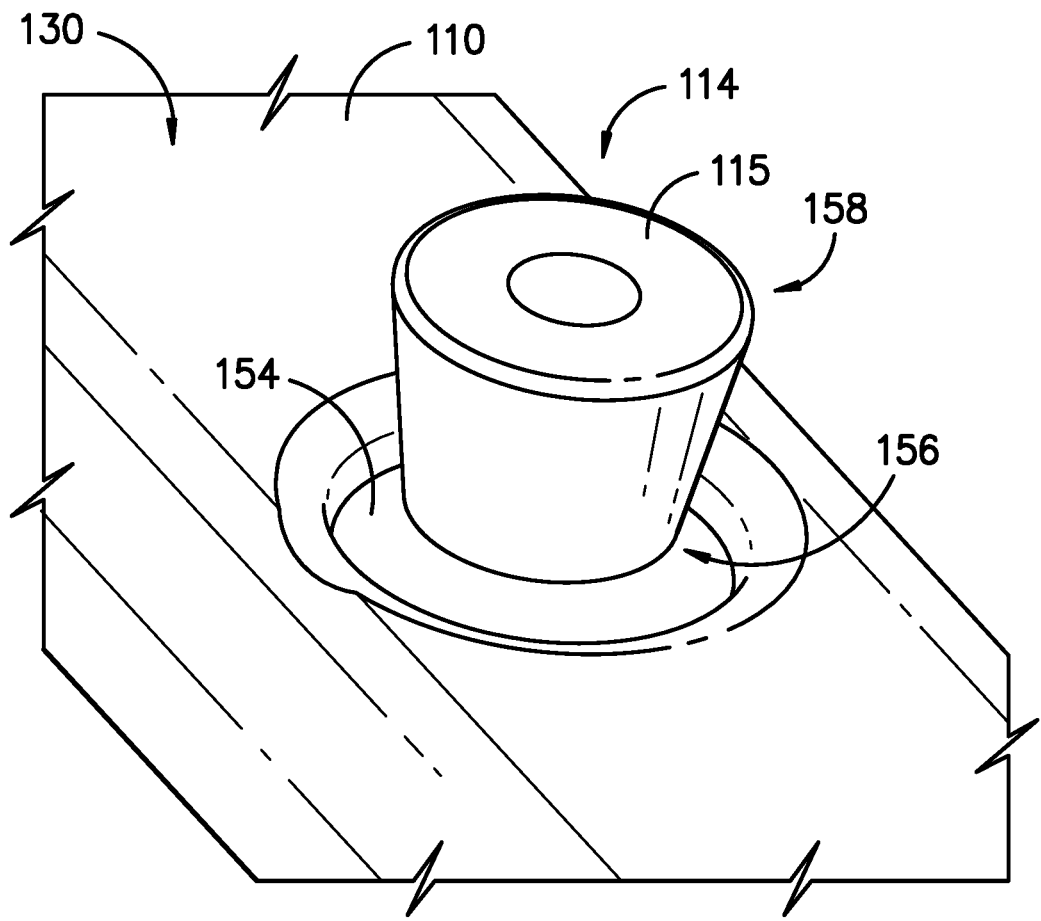
FIG. -10-

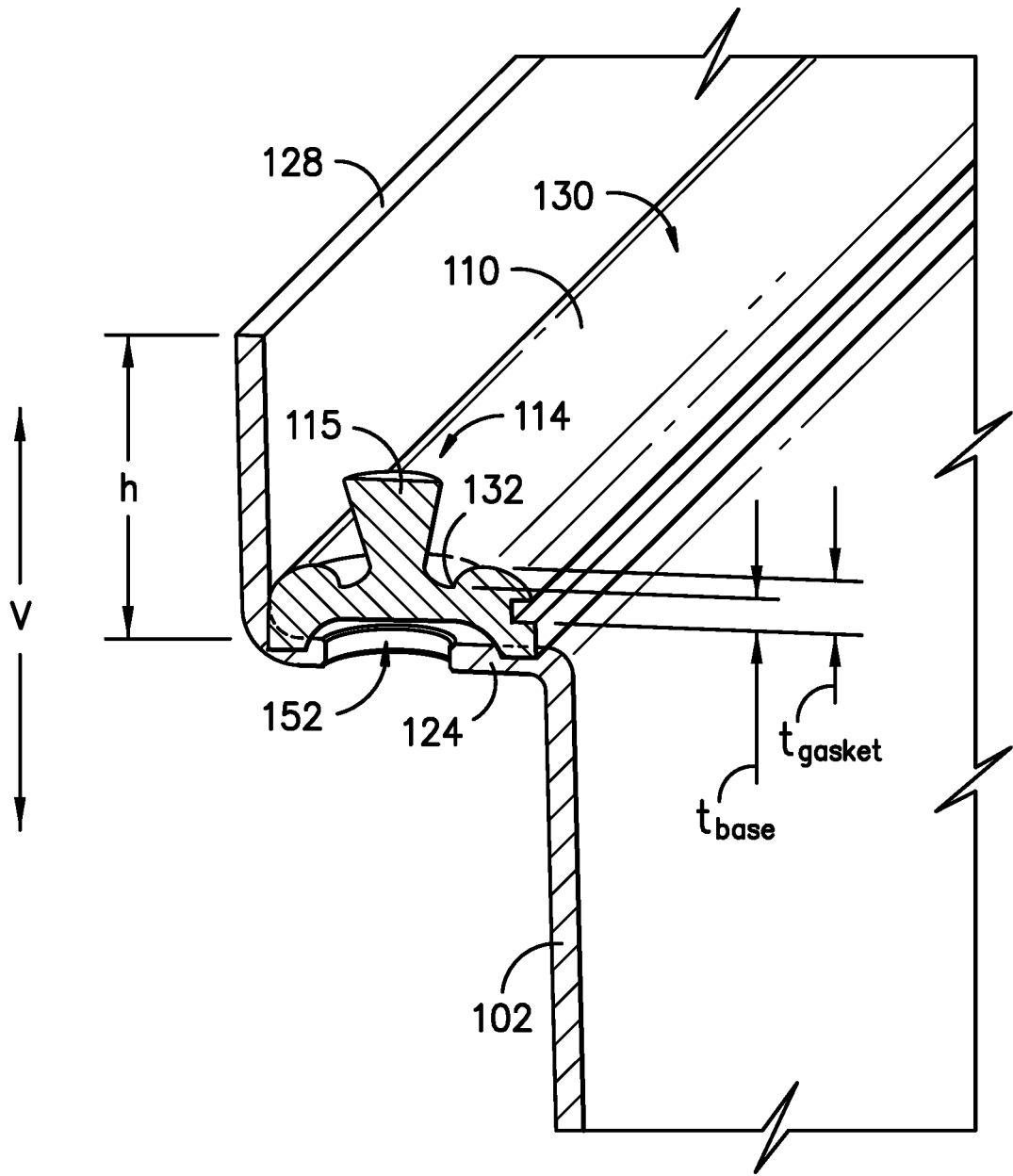
FIG. -11-

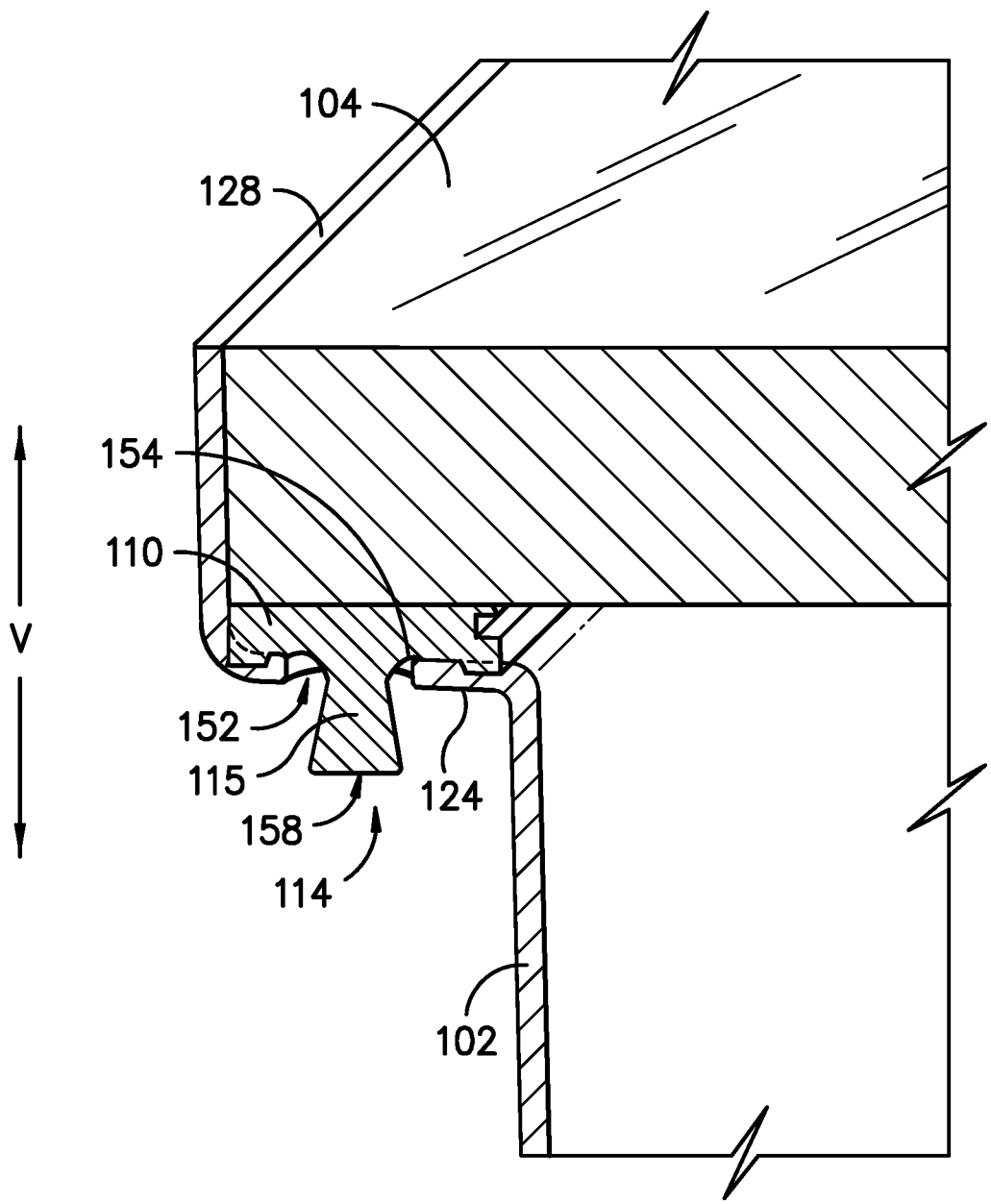
FIG. -12-

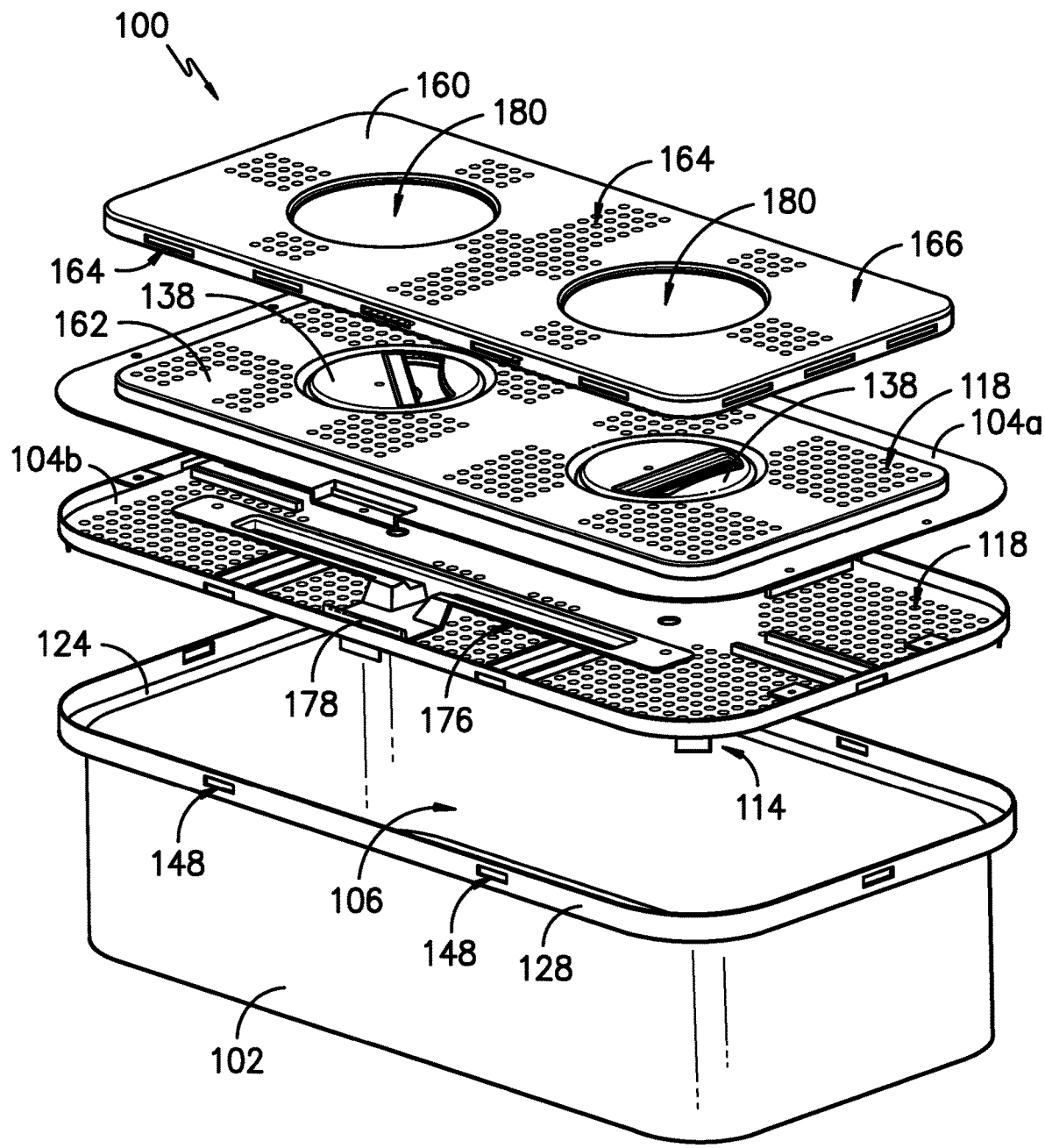
FIG. -13-

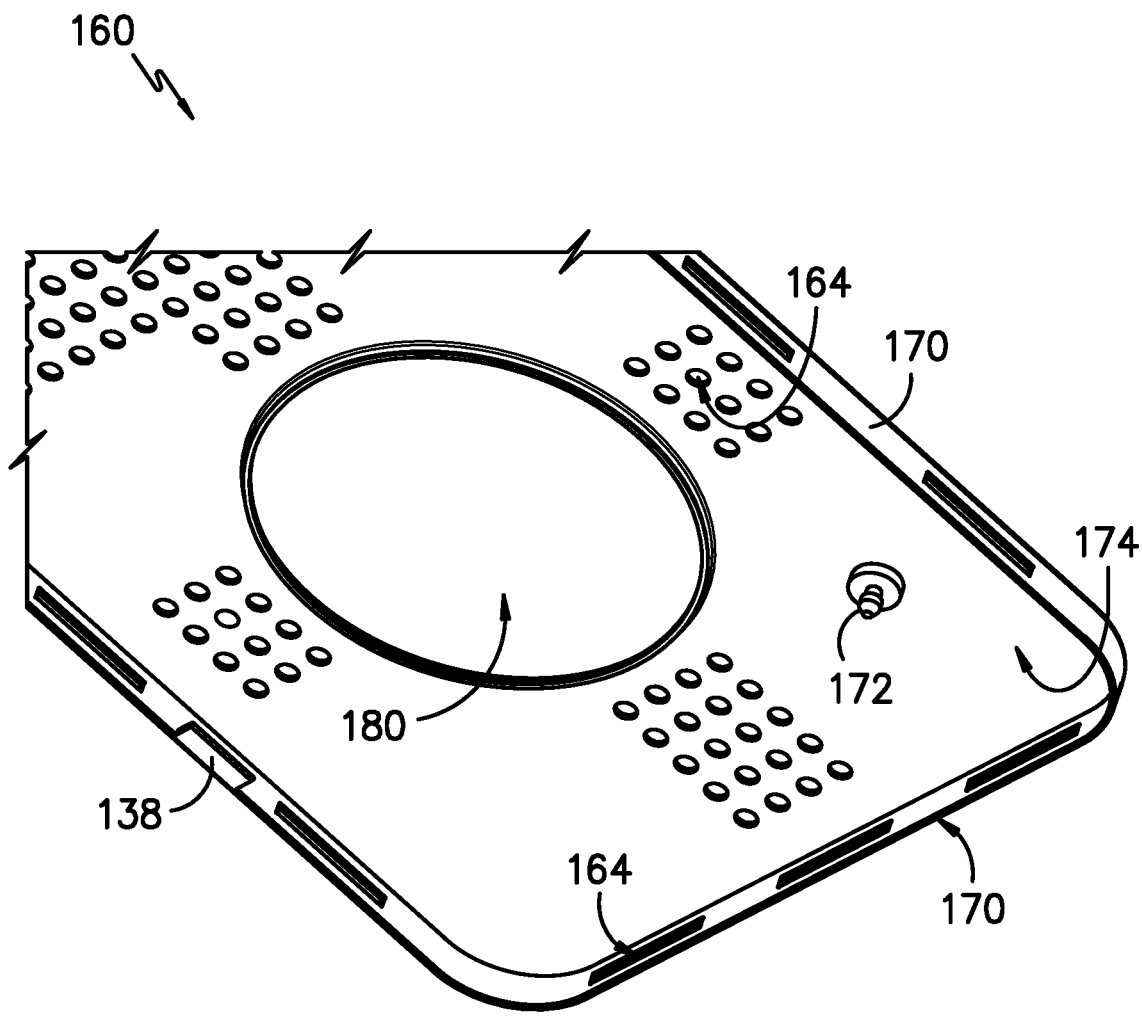
FIG. -14-

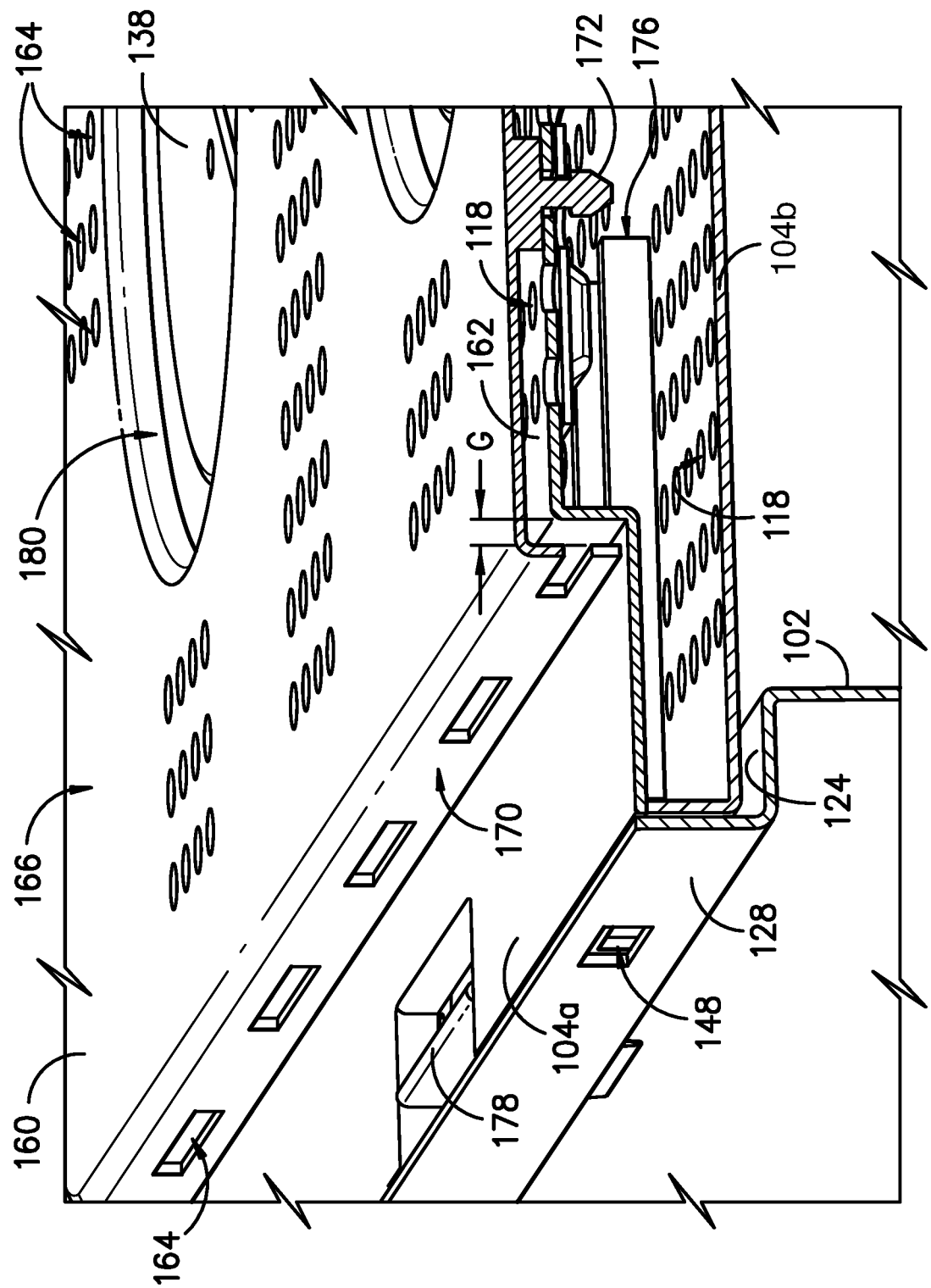

SEAL INTEGRITY INDICATOR FOR A STERILIZATION CONTAINER

CROSS-REFERENCE TO RELATED APPLICATIONS

The present application is a continuation of U.S. patent application Ser. No. 16/677,748 filed on Nov. 8, 2019, which claims priority to U.S. Provisional Application Ser. No. 62/757,870, filed Nov. 9, 2018, the contents of which are incorporated herein by reference.

FIELD

The subject matter of the present disclosure relates generally to sterilization containers and, more particularly, to rigid sterilization containers with features for indicating that the container is properly sealed.

BACKGROUND

Personnel in a sterilization station, such as the Central Service Room (CSR) or the Sterile Processing Department (SPD) of hospitals, are commonly charged with the responsibility of packaging surgical supplies to ensure that the sterility of the packaged contents is maintained from sterilization to the point of reuse. Several activities are involved in the task of sterile supply delivery to the operating room and other units, such as a cardiac catheterization lab, emergency room, labor and delivery room, intensive care unit, pediatric care unit, specialized burn care units, and other surgical or medical units.

Many of the surgical instruments and supplies used in an operating room (OR), or other surgical or medical unit, are reusable. These supplies typically include such things as clamps, scalpel blade handles, retractors, forceps, scissors, surgeon's towels, basins, and the like. All of these supplies must be collected after each procedure, decontaminated, washed and dried before placing into a sterilization packaging system, and sterilized before they can be used again in another procedure. The sterilization packaging systems used must be of the size and shape to accommodate the items to be sterilized, must be compatible with and withstand the physical conditions of the sterilization process, and must be capable of maintaining the sterility of their contents post-sterilization.

Typical means of sterilizing instruments include, among others, autoclaving with steam, exposure to ethylene oxide gas, and exposure to hydrogen peroxide plasma, as is done with the STERRAD® Sterilization System from Advanced Sterilization Products, Irvine, Calif. or as done with V-PRO® Low Temperature Sterilization Systems using Vaporized Hydrogen Peroxide (VHP®). After the package and its contents have been sterilized, the sterilization package typically is stored until it is needed for a surgical or other medical procedure.

Common sterilization packaging systems include sealable pouches, sterilization wraps, and rigid containers. As an example, a rigid sterilization container will permit the entry of sterilizing vapor/gas or other medium to sterilize the contents of the container while denying the ingress of contaminants such as bacteria and other infection causing materials or their vehicles after sterilization. As such, rigid sterilization containers generally provide a consistent barrier against the ingress of contaminants. Typical rigid containers have a base and a lid with a locking mechanism and a filtered port-opening, which may include natural or synthetic filter media (woven, non-woven, polytetrafluoroethylene (PTFE), etc.), valves, a MircoStop labyrinth, etc., where the sterilant ingresses and egresses, and a gasket usually is incorporated into the lid to help establish a seal between the lid and base. However, it is difficult to detect if the seal of typical rigid sterilization containers is properly formed. That is, with the seal gasket integrated within the sterilization container's lid, it is difficult to ascertain that the seal has properly formed for maintaining the sterility of the container contents post-sterilization. Further, it is difficult to detect if the seal gasket is damaged, which could hinder the gasket in the sterilization container from creating an adequate seal against contamination reaching of the contents. Therefore, without opening the container, one typically does not know if sterility has been maintained from when the sterilization container left the sterilization station to when the contents of the container are needed, e.g., in the OR.

Consequently, there is a need for a sterilization container that overcomes the shortcomings of known containers. In particular, an indicator for relatively quickly indicating to a user whether a sterilization container is or is not properly sealed, without requiring the user to open the container, would be advantageous. A sterilization container incorporating a visual seal indicator would be desirable. A sterilization container seal indicator that does not require a high compression force at the time of container closure to activate or deploy the seal indicator, to indicate that the container is sealed, also would be beneficial. Further, a seal indicator that does not require a high compression force for activation or deployment yet is not formed from a relatively low durometer material would be useful.

SUMMARY

The present invention provides sterilization containers with features for attaching a lid to a body of the container to seal a volume against an ingress of contaminants. The present disclosure also provides indicators for indicating whether a sterilization container is sealed against an ingress of contaminants. Additional aspects and advantages of the invention will be set forth in part in the following description, may be apparent from the description, or may be learned through practice of the invention.

In one aspect, the present subject matter is directed to a sterilization container. The sterilization container comprises a body that includes a first end, a second end opposite the first end, a first side extending between the first and second ends, and a second side opposite the first side and extending between the first and second ends. The body further includes an open top portion. The sterilization container also comprises a lid for securing to the body to close the open top portion of the body. The body and lid together defines an interior. The sterilization container further comprises a gasket for sealing the interior against an ingress of contaminants and a seal indicator for indicating a seal state of the sterilization container. The seal indicator comprises an invertible projection. The projection extends upward along a vertical direction in a first indicator state and extends downward along the vertical direction in a second indicator state. The projection is invertible from the first, upward position to the second, downward position. The first indicator state indicates an unsealed state of the sterilization container, and the second indicator state indicates a sealed state of the sterilization container.

In another aspect, the present subject matter is directed to a sterilization container. The sterilization container comprises a body that includes a first end, a second end opposite the first end, a first side extending between the first and second ends, and a second side opposite the first side and extending between the first and second ends. The body further includes an open top portion. The sterilization container also comprises a lid for securing to the body to close the open top portion of the body. The body and lid together define an interior. The sterilization container further comprises a gasket/filter including a gasket portion for sealing the interior against an ingress of contaminants and a filter portion extending across the open top portion of the body from the first end to the second end and from the first side to the second side. The gasket portion and the filter portion are integrally formed as a single piece component. Moreover, the sterilization container comprises a seal indicator for indicating a seal state of the sterilization container. The seal indicator comprises an invertible projection. The projection extends upward along a vertical direction in a first indicator state and extends downward along the vertical direction in a second indicator state. The projection is invertible from the first, upward position to the second, downward position. The first indicator state indicates an unsealed state of the sterilization container, and the second indicator state indicates a sealed state of the sterilization container. The seal indicator is formed in the gasket portion of the gasket/filter.

In still another aspect, the present subject matter is directed to a sterilization container that comprises a body and a lid that together define an interior. The body includes a first end, a second end opposite the first end, a first side extending between the first and second ends, and a second side opposite the first side and extending between the first and second ends. The body also includes an open top portion and a rim extending around the open top portion. The body further includes an inner lip defined around an inner surface of the body and recessed vertically inward such that the rim extends around the inner lip and has a vertical height h over the inner lip. Moreover, the lid has a closure mechanism that includes two rotatable handles and six arms. The six arms are configured to protrude through the lid and the body to secure the lid to the body. Each handle is in operative communication with three of the six arms such that the three arms move linearly when the handle is rotated. The sterilization container also comprises a gasket/filter that includes a gasket portion for sealing the interior against an ingress of contaminants and a filter portion extending across the open top portion of the body from the first end to the second end and from the first side to the second side. The gasket portion and the filter portion are integrally formed as a single piece component. The sterilization container further comprises a seal indicator for indicating a seal state of the sterilization container. The seal indicator comprises an invertible projection. The projection extends upward along a vertical direction in a first indicator state and extends downward along the vertical direction in a second indicator state. The projection is invertible from the first, upward position to the second, downward position. The first indicator state indicates an unsealed state of the sterilization container, and the second indicator state indicates a sealed state of the sterilization container. Further, the seal indicator is formed in the gasket portion of the gasket/filter, and the inner lip of the body is defined within the interior of the container. The lid is supported by the inner lip such that an inside edge of the lid is recessed within the body. Additionally, six rim openings are defined in the rim, and each rim opening is configured for receipt of a distal end of one of the six arms.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 provides a top, perspective view of a sterilization container according to an exemplary embodiment of the present subject matter.

FIG. 2 provides a top, perspective view of one end of the exemplary sterilization container of FIG. 1.

FIG. 3 provides a side view of one end of the exemplary sterilization container of FIG. 1.

FIG. 4 provides a side view of one end of a lid of the exemplary sterilization container of FIG. 1.

FIG. 5 provides a bottom view of the lid of the exemplary sterilization container of FIG. 1.

FIG. 6 provides a cross-section view of a portion of a closure mechanism in the lid of the exemplary sterilization container of FIG. 1.

FIG. 7 provides a top view of a body of the exemplary sterilization container of FIG. 1.

FIG. 8 provides a side, perspective view of the body of the exemplary sterilization container of FIG. 1.

FIG. 9 provides a top view of a combination gasket/filter of the exemplary sterilization container of FIG. 1, according to an exemplary embodiment of the present subject matter.

FIG. 10 provides a perspective view of a seal indicator projection extending from a gasket portion of the combination gasket/filter of FIG. 9.

FIG. 11 provides a cross-section view of the body and gasket portion of the combination gasket/filter of the exemplary sterilization container of FIG. 1 and exemplary combination gasket/filter of FIG. 9.

FIG. 12 provides a cross-section view of the body, with the lid secured thereto, and the gasket portion of the combination gasket/filter of the exemplary sterilization container of FIG. 1 and exemplary combination gasket/filter of FIG. 9.

FIG. 13 provides an exploded view of a sterilization container having a safety lid or cover according to an exemplary embodiment of the present subject matter.

FIG. 14 provides a perspective view of the underside or inner surface of the safety lid or cover of FIG. 13.

FIG. 15 provides a close-up view of a securing mechanism for the safety lid or cover of FIG. 13, where the securing mechanism is incorporated into a lid of the sterilization container.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Described herein are a sterilization packaging system or container and components thereof suitable for use in a variety of procedures for containing, sterilizing, storing, and using sterilized items such as surgical devices, instruments, or supplies. While described in conjunction with its use in surgical room procedures located in hospitals or ambulatory surgical facilities, the present subject matter is intended for use wherever there is a need for containerized sterilized devices, instruments, or materials. Consequently, the following description should not be considered a limitation as to the scope of use of the present subject matter.

Generally, the present subject matter provides indicators for indicating the integrity of a seal of the container. For example, described herein are seal indicators of sterilization containers that indicate whether the sterilization container is sufficiently sealed to prevent an ingress of contaminants into the container. If the container is sufficiently sealed, the seal indicator is in one state, and if the container is not sufficiently sealed, the seal indicator is in another state. In the first indicator state, the seal indicator is not visible to a user of the container from the exterior of the container, but in the second indication state, the seal indicator is visible from the exterior of the container. Thus, the state of the container is communicated to a user through the visibility of the seal indicator. That is, the seal indicator undergoes a change in state (i.e., a change in position relative to the exterior of the container) when the sterilization container transitions from not being sealed, e.g., when articles are being placed in the container for sterilization, to being sealed, e.g., when a lid of the container is properly secured to a body of the container, such that the user may be assured that the container is properly sealed to maintain sterility of the articles therein post-sterilization. Further, the seal indicator undergoes a visible change in state if the seal is broken after the lid is secured to the container, to signal to the user that the seal has been breached such that the articles in the container may no longer be sterile. As described herein, an exemplary seal indicator is integrally formed with a gasket of the sterilization container and comprises one or more invertible projections that are not visible from outside the container until a lid of the container pushes the projections until they invert and extend through corresponding openings in the container body. A reduced or decreased thickness of material at the area where each projection extends from the gasket, compared with the thickness of the remainder of the gasket, allows the projections to relatively easily invert from an upward position to a downward position. The seal indicators described herein may require a lower compression force to activate or deploy the seal indicator and provide increased flexibility in choosing an appropriate material durometer. Other features, such as color and shape of the projections, also may allow the seal indicator to be easily activated or deployed and to be more visible to a user of the sterilization container, increasing the ease of checking whether the container is properly sealed before and post-sterilization.

The present subject matter further provides a closure mechanism for closing and sealing a container against an ingress of contaminants. The present subject matter also provides a container having an inner lip in the body on which the lid and a gasket rest, as well as a combination gasket/filter in which the gasket and filter media are integrally formed as a single piece component. As described herein, a closure mechanism of the present subject matter is provided in the lid of a sterilization container and includes a rotatable handle and at least two arms that move linearly when the handle is rotated. The linear motion of the arms moves the arms into or out of engagement with the body of the container to secure the lid to the body. Further, engagement of the arms with the body compresses the gasket, which may be part of a combination gasket/filter disposed within the body on an inner lip such that the gasket is disposed between the lid and the body, to seal an interior of the container and thereby provide a barrier preventing contaminants such as bacteria or the like from entering the interior. The inner lip thus provides a shelf on which the gasket and lid rest such that the gasket and lid are recessed within the body. As such, an inside edge of the lid is recessed within the body and, therefore, may be aseptically presented when the container is opened after undergoing a sterilization process, which includes delivery of a sterilization agent such as steam, ethylene oxide, hydrogen peroxide plasma, etc. to the container interior. Moreover, the number of arms of the closure mechanism may be selected such that the arms are distributed about the perimeter of the lid to provide an even or uniform closure force on the gasket, which may help provide a more uniform and better seal between the lid and body of the container. The present subject matter also provides various methods for sealing a sterilization container and for indicating a seal state of a sterilization container.

Referring now to the figures, FIG. 1 provides a top, perspective view of a sterilization container 100 according to an exemplary embodiment of the present subject matter. FIG. 2 provides an end, perspective view of a portion of the exemplary sterilization container 100. FIG. 3 provides a side view of a portion of the sterilization container 100. FIGS. 4-6 provide various views of a lid of the sterilization container. FIG. 7 provides a top view of a body of the sterilization container, and FIG. 8 provides a side, perspective view of the body.

As shown in FIGS. 1 through 3, the sterilization container 100 comprises a body 102 and a cover or lid 104. Together, the body 102 and lid 104 define an interior 106 (FIGS. 7, 8) of the container 100. One or more articles, e.g., clamps, scalpel blade handles, retractors, forceps, scissors, surgeon's towels, basins, and like surgical devices, instruments, or supplies, may be placed in the interior 106 of the container 100 for sterilization such that, e.g., the article(s) may be reused in another procedure. The body 102 and the lid 104 can be reusable and can be formed from a rigid material such stainless steel, anodized aluminum, polyetheretherketone (PEEK), polyaryletherketone, polyphenylsulphone (PPSU), polysulphone (PSU), filled PPSU, and filled PSU. Once sealed, as described in greater detail herein, the container 100 can then be transferred to sterilizing equipment and exposed to sterilization conditions as generally known in the art. Such sterilization conditions can include, for example, steam, ethylene oxide, or hydrogen peroxide plasma sterilization conditions. Sterilization conditions are the conditions present during a particular sterilization methodology utilized that substantially kills or completely destroys bacteria and other infectious organisms in an industrial or medical product to the desirable sterility assurance level (e.g., $\geq 10^{-6}$ log reduction for terminal sterilization).

In FIGS. 1-3, the sterilization container 100 is closed and sealed against an ingress of contaminants. That is, the body 102 includes an open top portion 108, but when the lid 104 is secured to the body 102 as shown in FIGS. 1-3, the lid 104 covers the open top portion 108 of the body 102 and a gasket 110 (FIGS. 9-12) is compressed between the lid 104 and body 102, providing a continuous sealing interface between the lid 104 and body 102 to seal the container 100 against an ingress of contaminants, as described in greater detail herein. For instance, the gasket 110 is disposed between the body 102 and lid 104 and extends about a perimeter of the body 102 and lid 104. The gasket 110 may be formed from polyurethane, silicone, polyvulcanate, polyvinylidene chloride (PVDC), polytetrafluoroethylene (PTFE), polysulphones, crosslinked elastomers, etc. In FIGS. 7 and 8, the sterilization container 100 is open and, thus, is unsealed or not sealed against the ingress of contaminants. More specifically, the lid 104 is separated from the body 102 to expose the interior 106 of the container 100.

The container 100 includes one or more handles 112 attached to the body 102 for lifting, carrying, or otherwise handling the container 100. For example, as illustrated in FIG. 2, a first handle 112 may be attached to a first end 102a of the body 102, and a second handle 112 may be attached to a second end 102b of the body 102, where the second end 102b is opposite the first end 102a. In other embodiments, the first handle 112 may be attached to a first side 102c of the body 102, and the second handle 112 may be attached to a second side 102d of the body 102, where the second side 102d is opposite the first side 102c and the first and second sides 102c, 102d extend between the first and second ends 102a, 102b. Other configurations and/or placements of one or more handles 112 may be used as well. Additionally, it will be appreciated that the sterilization container 100 need not have a generally rectangular shape as shown in FIG. 1, but the container 100 may have any appropriate shape for containing items to be sterilized.

As further depicted in FIG. 3, a visual seal indicator 114 provides a visual indication of a seal state of the sterilization container 100. For instance, the seal indicator 114 indicates to a user of the container 100 whether the container 100 is in a first, unsealed state, where the container 100 is not sealed against an ingress of contaminants (i.e., contaminants could enter the container 100), or a second, sealed state, where the container 100 is sealed against the ingress of contaminants (i.e., contaminants cannot enter the container 100). That is, the seal indicator 114 is a binary indicator of the integrity of the seal between the body 102 and lid 104 of the container 100, e.g., the indicator 114 indicates when the seal is established and when the seal is broken or otherwise compromised. More particularly, the seal indicator 114 has a first indicator state that indicates the unsealed container state and a second indicator state that indicates the sealed container state. The seal indicator 114 is visible to a user of the container 100 from an exterior 116 of the container 100 to signal to the user whether the container is sealed or unsealed. A change in state, i.e., from the first indicator state to the second indicator state or from the second indicator state to the first indicator state, may be achieved by a change in color, shape, size, position, etc. of the seal indicator 114 to signal the container 100 has transitioned from its unsealed state to its sealed state or from its sealed state to its unsealed state.

As described in greater detail herein, the seal indicator 114 is configured to not be visible (or to be invisible) in the first indicator state and is configured to be visible in the second indicator state. That is, one cannot see the seal indicator 114 from the exterior 116 of the container 100 until the container 100 is sealed against the ingress of contaminants. The seal indicator 114 may be a different color than the body 102 and/or lid 104 of the container 100, and the color of the seal indicator 114 may be selected such that there is a high contrast between the color of the seal indicator 114 and the color(s) of the remainder of the sterilization container 100, and/or the color may be selected to reinforce the signal communicated by the color. For example, in an exemplary embodiment, the seal indicator 114 is red and the lid 104 and body 102 of the container 100 are both silver or gray such that there is a high contrast between the seal indicator 114 and the remainder of the container 100, which may improve the visibility of the seal indicator 114 when the container 100 is sealed. Other high contrast or bright colors may be used to improve the visibility of the seal indicator 114 against the container 100 when the seal indicator 114 is outside of the container 100 to signal the sealed container state. In another embodiment, the seal indicator 114 is green to reinforce the signal that the container 100 is sealed against the ingress of contaminants. Thus, the exemplary seal indicator 114 indicates a change in the seal state of the container 100 through a change in position, which may be reinforced or highlighted by the color of the seal indicator 114 compared to the color of the remainder of the container 100.

As shown in the figures, in some embodiments, the seal indicator 114 is visible from the exterior 116 of the container 100 through an indicator opening 152 in the body 102. In exemplary embodiments, a plurality of openings 152 are defined in the body 102 and/or lid 104 such that the seal indicator 114 is visible from each of the first end 102a, the second end 102b, the first side 102c, and the second side 102d of the body 102. The seal indicator 114 is described in greater detail below.

The seal between the body 102 and the lid 104 is established by the gasket 110. The gasket 110 provides an air tight seal between the body 102 and lid 104 and, thus, seals the interior 106 of the container 100 against the ingress of contaminants. That is, the gasket 110 extends between the body 102 and lid 104. Securing the lid 104 to the body 102 compresses the gasket 110 between the body 102 and lid 104 to seal the interior 106. When the gasket 110 is not compressed, or not fully compressed, such that the interior 106 is not sealed against the ingress of contaminants, the container 100 is in its first, unsealed state and the seal indicator 114 is in its first indicator state, i.e., the seal indicator 114 is not visible from the exterior 116 of the container 100. Similarly, when the gasket 110 is fully compressed, such that the interior 106 is sealed against the ingress of contaminants, the container 100 is in its second, sealed state and the seal indicator 114 is in its second indicator state, i.e., the seal indicator 114 is visible from the container exterior 116.

Moreover, as shown in FIGS. 1, 2, 5, and 6, the lid 104 defines one or more vents 118 of the sterilization container 100. More particularly, the vents 118 in the illustrated embodiment are openings in a top surface 105 of the lid 104. In other embodiments, the vents 118 may be openings in one or more side surfaces 107 of the lid 104, where the side surfaces 107 are orthogonal to the top surface 105; openings in the body 102; or openings in both the lid 104 and the body 102. A filter 120 is positioned within the sterilization container 100 adjacent the vent(s) 118 to prevent contaminants from entering the interior 106. The vent(s) 118 and filter 120 permit fluids, such as air, steam, and chemical sterilization agents, to pass through the lid 104 and into the interior 106 of the sterilization container 100, e.g., to sterilize the contents of the container 100, as well as to pass from the interior 106 to an exterior environment, e.g., to help the contents of the container 100 dry after a sterilization process.

The filter 120 may be, for example, a sheet of material that extends over the open top portion 108 of the body 102 such that the filter 120 is positioned between the lid 104 and the container interior 106. That is, as illustrated in the figures, the filter 120 extends across the open top portion 108 of the body 102 from the first end 102a to the second end 102b and from the first side 102c to the second side 102d. However, the filter 120 need not be configured as a sheet but may have any suitable configuration or construction. For instance, as described in greater detail herein, the filter 120 and gasket 110 may be integrally formed as a single component, which may be referred to as a combination gasket/filter 122. Further, the filter media 120 of the combination gasket/filter 122, can be made from a number of materials and, generally, may be made of a material from one of two main classes, reusables and disposables. Reusables are materials that, as the name suggests, can be reused, typically by washing or some other form of cleaning. Disposables, on the other hand, usually are one-use items that are discarded or recycled after their initial use. Generally, cloth, linen, or other woven materials fall into the reusable category while disposables normally include nonwoven materials made from either or both natural and synthetic fibers such as paper, fibrous polymeric nonwovens, and films (e.g., PTFE porous films or membranes), which are capable of passing sterilants and retarding transmission of bacteria and other contaminants.

Nonwoven sterilization materials present several advantages due to their barrier properties, economics, and consistent quality. The nonwoven materials can be made from a variety of processes including, but not limited to, air laying processes, wet laid processes, hydroentangling processes, spunbonding, meltblowing, staple fiber carding and bonding, and solution spinning. The fibers themselves can be made from a variety of both natural and synthetic materials including, but not limited to, cellulose, rayon, nylon, polyesters, polyolefins, and many other materials. The fibers may be relatively short, staple length fibers, typically less than three inches, or longer and substantially more continuous fibers such as are produced by spunbonding and meltblowing processes. Whatever materials are chosen, the resultant filter material must be compatible with the particular sterilization technique being used and must also provide both strength and barrier properties to maintain the sterile nature of the contents of the sterilization container 100 until use.

In some embodiments, the lid 104 may define a window through which the filter or filter media 120 is visible to a user of the container 100, and the filter may also define a window, formed from a transparent breathable film, or the like that still provides a barrier against contaminants, that aligns with the window in the lid 104 such that the user can see through the filter and into the interior 106 of the container 100. Such a window allows the user to, e.g., verify contents of the container 100, reducing the need to open containers to find specific instrument sets, as well as view any internal indicators, if provided, which may be indicators of seal integrity or whether the container 100 has undergone a sterilization process. However, in other embodiments, the filter or filter media 120 may be made from a translucent or opaque material, such as, e.g., an SMS material, polytetrafluoroethylene (PTFE), paper, or the like. For example, polyolefin-based fibers and their resultant nonwovens are particularly well-suited for the production of a flexible filter, and a polypropylene spunbonded nonwoven can be used to impart strength characteristics to the filter. In some embodiments, the filter may be made from laminates such as a laminate of spunbonded and meltblown or spunbonded, meltblown, spunbonded to impart both strength and barrier properties to the filter. A spunbonded-meltblown-spunbonded (SMS) material is made from three separate layers that are laminated to one another. The method of making these layers is known and described in U.S. Pat. No. 4,041,203 to Brock, et al., which is incorporated herein in its entirety by reference. The material of Brock, et al. is a three layer laminate of spunbonded-meltblown-spunbonded layers. The two outer layers of SMS are a spunbonded material made from extruded polyolefin fibers, or filaments, laid down in a random pattern and then bonded to one another. The inner layer is a meltblown layer also made from extruded polyolefin fibers generally of a smaller diameter than the fibers in the spunbonded layers. As a result, the meltblown layer provides increased barrier properties due to its fine fiber structure, which permits the sterilizing agent to pass through the fabric while preventing passage of bacteria and other contaminants. Conversely, the two outer spunbonded layers provide a greater portion of the strength factor in the overall laminate. The laminate may be prepared using an intermittent bond pattern that is preferably employed with the pattern being substantially regularly repeating over the surface of the laminate. The pattern is selected such that the bonds may occupy about 5% to about 50% of the surface area of the laminate. Desirably, the bonds may occupy about 10% to about 30% of the surface area of the laminate. In an exemplary embodiment, the filter is made from an SMS material, but the filter also may be made from other suitable materials.

Further, in some embodiments, structural support can be provided to the filter media 120, e.g., in the form of a plurality of longitudinal support members extending in a longitudinal direction L and a plurality of transverse support members extending in a transverse direction T, which are disposed on an upper surface of the filter media 120. However, it is to be understood that, alternatively, the longitudinal support members and/or the transverse support members can be disposed on a lower surface of the filter media 120. Such an arrangement of support members, which form a grid across the surface of the filter media 120, can provide the filter media 120 with improved structural durability. In addition, it is to be understood that the structural support can take any suitable shape or form and is not limited to the longitudinal support members and transverse support members as described. For instance, the structural support can be in the form of a metal mesh or grid that is incorporated into the filter media 120 itself.

In still other embodiments, the filter component of the combination gasket/filter 122 can be a corrugated sheet of filter material 120. The corrugated filter media 120 includes a plurality of peaks and valleys. Such a geometry can increase filtration efficiency and provide increased structural robustness to the filter component of the gasket/filter 122.

As previously described, in the exemplary embodiment of the sterilization container 100, the gasket 110 and filter 120 are integrally formed as a single piece component, a combination gasket/filter 122. Thus, the gasket forms a gasket portion 110 of the gasket/filter 122 and the filter or filter media forms a filter portion 120 of the gasket/filter 122. In the exemplary embodiment shown in FIG. 9, the gasket portion 110 of the combination gasket/filter 122 defines the outermost boundary of the combination gasket/filter 122 and completely surrounds the filter media 120. The gasket portion 110 of the combination gasket/filter 122 may be wider than typical sterilization container gaskets, and as shown in FIGS. 7 and 8, an inner lip 124 of the body 102, which is the portion of the body 102 against which the gasket portion 110 rests, also may be wider than a surface that would normally contact a sterilization container gasket. As such, the body 102 and the gasket portion 110 of the gasket/filter 122 have an increased contact area compared to typical sterilization containers, thereby forming a more tortuous path for contaminants to enter the container interior 106. Other advantages arising from having the inner lip 124 as the contact area for the gasket portion 110 of the combination gasket/filter 122 are discussed herein.

Further, because the combination gasket/filter 122 is formed as a single piece component and the gasket/filter 122 completely covers the open top end 108 of the body 102 as shown in the figures, interfaces between mating parts can be minimized, even when including a transparent film to form a window into the interior 106. For example, a combination gasket/filter 122 eliminates separate interfaces between the lid 104 and filter 120 and the lid 104 and gasket 110. Minimizing the number of interfaces helps reduce the opportunity for contamination breach, i.e., a breach of the seal by bacteria or other organisms or substances that could compromise the sterility and safety of the articles within the container 100. Moreover, the combination gasket/filter 122 allows for a single use gasket 110, which eliminates wear and tear to the gasket 110 that arises from reusing the gasket in additional opening/closing cycles and sterilization cycles. That is, it may be desirable for the gasket/filter 122 to be a disposable, single use component of the container 100, e.g., to reduce the opportunity for seal breach due to wear of the gasket 110. Thus, in some embodiments, a new, single use gasket/filter 122 may be used with a reusable body 102 and lid 104 each time the container 100 is used to sterilize one or more articles. Of course, other components of the sterilization container 100 also may be configured as single use components. However, in some embodiments, the gasket/filter 122 may be configured to be reusable. For instance, although the gasket/filter 122 can be a disposable, single use component, e.g., to eliminate the risk of wear and tear on the gasket portion 110 that can result in inadequate sealing capabilities, in some embodiments, the gasket portion 110 can be formed from a reusable material that is more durable, such as elastomeric silicone, polytetrafluoroethylene, polyvinylidene fluoride, polyurethane, a polyolefin (e.g., polyethylene or polypropylene) that can withstand multiple sterilization cycles without losing their compressibility. Further, as previously described, the filter portion 120 may be formed from a material selected from a class of reusable filter materials, such that the combination gasket/filter 122 is a reusable component of the sterilization container assembly. As described herein, the body 102 and lid 104 also may be reusable components of the assembly and may be formed from appropriate materials for providing a rigid container that can withstand multiple sterilization cycles and repeated handling and loading with articles for sterilization.

Additionally, the single piece gasket/filter 122 simplifies assembly and use by a user of the container 100. For example, a single piece gasket/filter 122 is easier to assemble with the body 102 and lid 104 than a separate gasket and one or more filters, which also could require filter retainers or the like to hold them in position. Thus, the reduced number of parts helps simplify assembly of the container 100. Similarly, a single piece gasket/filter 122 is easier to remove than multiple pieces, thereby simplifying the opening of the container 100.

As already mentioned, the body 102 defines an inner lip 124 around an inner surface 126 of the body 102 within the interior 106 of the container 100 such that the inner lip 124 is configured as a shelf within the container 100. Further, the inner lip 124 is recessed vertically inward with respect to a rim 128 of the body 102. That is, the rim 128 extends at a height h over the inner lip 124 defined around the inner surface 126 of the body 102. As such, the components of the sterilization container 100 that are disposed on or supported by the inner lip 124 are at least partially recessed with the body 102 of the container 100.

As shown in FIGS. 1-3, the lid 104 is configured to be supported by the inner lip 124 such that the lid 104 is recessed within the body 102, i.e., the lid 104 (the top portion of the container 100) fits within the body 102 (the bottom base portion of the container 100). Further, the gasket portion 110 of the combination gasket/filter 122 is disposed on the inner lip 124 such that the gasket portion 110 is disposed between the lid 104 and the inner lip 124. The lid 104 contacts an upper surface 130 of the gasket portion 110 of the gasket/filter 122, and the body 102, at the inner lip 124, contacts a lower surface 132 of the gasket portion 110. The gasket portion 110 is compressible by a closing force, such as a force on the lid 104 as described in greater detail herein, and interacts with the inner lip 124 to form an interface or mating surface between each of the lid 104 and gasket portion 110 and the body 102 and gasket portion 110. Further, the gasket portion 110 is designed to conform to and fit with the inner lip 124 to provide an adequate barrier seal when the container 100 is closed. Thus, the sealing interface between the body 102 and lid 104, which is at the gasket portion 110 of the gasket/filter 122 that contacts each of the body 102 and lid 104, is inside or internal to the container 100, i.e., the body rim 128 separates the sealing interface from the environment external to the container 100. Accordingly, an inner or inside edge 134 of the lid 104 (FIG. 5) is closed, sealed, and not exposed to the exterior 116 of the container 100. As such, the inside edge 134 is not exposed to the external environment after sterilization and, thus, should be considered free of potential microbial containments associated with the environment. Hence, the inside edge 134 of the lid 104 can be aseptically presented when the lid 104 is opened and removed from the body 102 to expose the sterilized contents contained within the container 100 in the operating room, cardiac catheterization lab, emergency room, labor and delivery room, intensive care unit, pediatric care unit, specialized burn care unit, or any other surgical or medical unit. Moreover, providing the sealing interface between the body 102 and lid 104 at the inside or interior of the container 100 (i.e., along the inner lip 124) makes the gasket 110 and the sealing surfaces of the lid 104 and body 102 (i.e., the surfaces of the lid 104 and body 102 that contact the gasket 110) less prone to damage, e.g., during transportation of the container 100, which helps keep the seal secured during handling and storage of the container 100.

Referring now to FIGS. 1-4 and 6, the exemplary sterilization container 100 also includes a closure mechanism 136 that provides the force required to close and seal the container 100 against the ingress of contaminants. The closure mechanism 136 is part of the lid 104 and includes at least one rotatable handle 138 and at least two arms 140. The at least two arms 140 are configured to protrude from the lid 104 and through body 102 to secure the lid 104 to the body 102. That is, the arms 140 resist upward motion of the lid 104, holding the lid 104 in position with respect to the body 102. Further, the handle 138 is in operative communication with the at least two arms 140 such that the arms 140 move or translate linearly when the handle 138 is rotated. For example, the closure mechanism 136 may comprise a cam 142 connected to the rotatable handle 138 that contacts the arms 140 as the handle 138 is rotated to transfer the motion of the handle 138 to the arms 140. The arms 140 move linearly to engage or disengage the body 102 to secure or unsecure the lid 104 with respect to the body 102. In some embodiments, the closure mechanism 136 may incorporate one or more features that provide feedback to a user that the closure mechanism 136 is fully engaged. For example, as shown in FIG. 6, the closure mechanism 136 includes ball plungers 143, which provide audible feedback (with a "click" or other such sound) when the cam 142 is fully engaged, thereby indicating the arms 140 are engaged with the body 102. As another example, the closure mechanism 136, e.g., the handle 138, may lock into place once the cam 142 is fully engaged, which provides tactile feedback to the user that the cam 142 and arms 140 are fully engaged. Other features, such as colored distal ends of the arms 140 as described below, also may be used to signal to the user that the cam 142 and closure mechanism 136 is fully engaged.

In the depicted embodiment, each handle 138 is generally circular in shape and is received in a complementary shaped recess 144 in the lid 104. A first portion 138a of each handle 138a is pinned to a second portion 138b of the handle 138 such that the first portion 138a is pivotable toward and away from the lid 104. The first portion 138a of each handle 138 defines an opening 146, e.g., for a user to slide his or her fingers into to grasp and rotate the handle 138. The first portion 138a of each handle pivots up or away from the lid 104 to be in position for the user to grasp and rotate the handle 138, while the second portion 138b is connected to the cam 142 to translate the rotating motion of the handle 138 to the arms 140 in operative communication with the respective handle 138. The first portion 138a of each handle 138 pivots down or toward the lid 104 when the handle 138 is not in use, and each handle 138 may be completely recessed within its respective recess 144 when not in use, e.g., to reduce the height of the container 100 (such that it better fits in a storage area, etc.), to not impede stacking of another sterilization container on top of the container 100, to protect the handles 138, etc. It will be appreciated that the handle(s) 138 and recess(es) 144 also may have shapes other than generally circular.

In some embodiments, the container 100 may include one rotatable handle 138 and two linearly translating arms 140, such that two points of force are applied to the lid 104 to hold it in position with respect to the body 102 and to compress the gasket portion 110 of the gasket/filter 122 to seal the container interior 106. In other embodiments, the container 100 may include one rotatable handle 138 and four linearly translating arms 140, thereby providing two additional points of force (for a total of four) on the lid 104. Alternatively, the container 100 may include two rotatable handles 138 and four linearly translating arms 140, such that each handle 138 controls two arms 140. In the illustrated exemplary embodiment, the container 100 includes two rotatable handles 138 and six linearly translating arms 140, thereby providing two additional points of force on the lid 104 over the prior example (for a total of six points of force on the lid 104). Each handle 138 in the exemplary embodiment is in operative communication with three arms 140a, 140b, 140c. Other numbers of handles 138 and arms 140 may be used as well. In embodiments employing two or more handles 138, the action of the handles 138 may be linked, such that turning one causes all arms 140 to move linearly, or may be separate, such that turning one handle 138 causes only a portion of the arms 140 to move linearly.

An increase in the number of points at which force is applied to the lid 104 improves the distribution of the closing force on the lid 104 and allows more uniform sealing. More specifically, typical sterilization containers apply force to the lid at the ends of the lid, e.g., through a latch that engages the lid to hold it in position with respect to the body, with no force directly applied at the sides of the lid. Thus, applying force at four, six, or any number of points greater than two increases the distribution of the force about the lid 104 compared to typical sterilization containers. By evenly spacing the arms 140 about the perimeter of the container 100, including the ends 102a, 102b, and sides 102c, 102d as shown in the illustrated embodiment, the force can be applied evenly about the container 100. A more evenly distributed force allows sealing between the lid 104 and body 102, via the gasket portion 110 of the gasket/filter 122, to be more uniform about the contact area between the body 102, gasket 110, and lid 104. More uniform sealing better ensures a complete seal between the lid 104 and body 102.

Referring now to FIGS. 7 and 8, the body 102 defines several openings therein, including in the inner lip 124 and the vertical wall of the rim 128. First, referring particularly to FIG. 8, the body 102 defines at least two arm openings 148 in the rim 128. Each arm opening 148 receives a distal end 150 of an arm 140 of the closure mechanism 136 when the closure mechanism 136 is manipulated to secure the lid 104 to the body 102. That is, as previously described, the distal ends 150 of the at least two arms 140 of the closure mechanism 136 protrude from the lid 104 through rim openings 148 in the body 102 when the at least one handle 138 is rotated to cause the arms 140 to move linearly outward. In the depicted exemplary embodiment, the rim 128 of the body 102 defines six rim openings 148, one for each of the six arms 140 of the exemplary closure mechanism 136. It will be understood that the rim 128 may define a number of rim openings 148 that corresponds to the number of arms 140 of the closure mechanism 136 of the lid 104. Further, in some embodiments, at least the distal end 150 of each arm 140, which protrudes through a rim opening 148, may have a color or may be colored to contrast with the remainder of the sterilization container 100 to signal that the lid 104 is closed. That is, at least the distal end 150 of each arm 140 has a color that contrasts with a color of the lid 104 and a color of the body 102 such that, e.g., the distal ends 150 are more visible to a user of the container 100 when engaged with the body 102, thereby better signaling that the closure mechanism 136 is engaged and the container 100 is closed. For instance, the distal ends 150 may be the same color as the seal indicator 114, such as red or green as previously described, or the distal ends 150 may be a different color from the seal indicator 114 as well as the remainder of the sterilization container 100.

Second, referring particularly to FIG. 7, the body 102 defines a plurality of indicator openings 152 in the inner lip 124. The indicator openings 152 allow the seal indicator 114 to protrude through the inner lip 124 to indicate the lid 104 is secured to the body 102 and the gasket 110 is sufficiently compressed to seal the container interior 106 against the ingress of contaminants. More specifically, the seal indicator 114 may be formed as part of the gasket portion 110 of the gasket/filter 122, as illustrated in FIG. 9. For example, the seal indicator 114 may comprise one or more invertible projections 115 that have a first position and a second position and are formed with the gasket portion 110; six projections 115a, 115b, 115c, 115d, 115e, 115f extend from the gasket portion 110 in the depicted embodiment. In the second position, the projections 115 are inverted, or upside down or in the opposite position, compared to the first position. Thus, in the first position, the projections 115 project or extend upward along the vertical direction V and are not visible outside the container 100, but in the second position, the projections 115 project or extend downward along the vertical direction V. The indicator openings 152 are defined in the inner lip 124 of the body 102 to correspond to the seal indicator projections 115a-115f; thus, the inner lip 124 defines six indicator openings 152a, 152b, 152c, 152d, 152e, 152f. When in their second, downward position, each projection 115 extends through a corresponding indicator opening 152 such that the projection 115 of the seal indicator 114 is visible from the container exterior 116, i.e., outside the container 100.

As illustrated in FIGS. 10 and 11, the seal indicator 114 is in the first indicator state when the lid 104 is not secured to the body 102 and the gasket portion 110 is not compressed to seal the sterilization container 100 against the ingress of contaminants. Thus, each seal indicator projection 115 is in its first, upward position such that the seal indicator 114 is not visible from the exterior 116 of the container 100. However, as shown in FIG. 12, when the lid 104 is received on the inner lip 124 and the closure mechanism 136 is engaged to secure the lid 104 to the body 102 and compress the gasket portion 110 of the gasket/filter 122 between the lid 104 and body 102 to seal the container interior 106, the seal indicator 114 is in the second indicator state and each projection 115f is in its second, downward position, extending through a corresponding indicator opening 152 such that the seal indicator 114 is visible from the container exterior 116. The seal indicator projections 115 may be defined along the gasket portion 110 and the indicator openings 152 may be defined along the inner lip 124 such that at least one projection 115 of the seal indicator 114 is visible from each end 102a, 102b and side 102c, 102d of the body 102 when the seal indicator projections 115 extend through the indicator openings 152. For example, referring to FIGS. 7-9, the indicator openings 152a, 152c, 152d, 152f are defined in the corners of the inner lip 124, and indicator openings 152b, 152e are defined in the inner lip 124 about midway along the respective side 102c, 102d of the body 102. Similarly, the projections 115a, 115c, 115d, 115f are defined in the corners of the gasket portion 110, and the projections 115b, 115e are defined approximately midway along the respective side of the gasket/filter 122. As such, the indicator openings 152 are defined in the inner lip 124 to correspond to the locations of the projections 115 along the gasket portion 110 of the gasket/filter 122. Therefore, the seal indicator 114 may be visible from each end and side of the sterilization container 100 such that a user can ascertain from viewing any end or side of the container 100 whether the container 100 is properly sealed and/or the seal has not been compromised. It will be understood that only the gasket portion 110 of the combination gasket/filter 122 is shown; the filter portion 120 is omitted for clarity. Of course, in some embodiments, the gasket 110 and filter 120 may be separate components (rather than a combination gasket/filter), and the gasket 110 in such embodiments may be configured as shown in FIGS. 10-12.

As further illustrated in FIGS. 9-12, each projection 115 has a generally conical shape. Each indicator opening 152 may have a shape complementary to a cross-sectional shape of the projections 115. Accordingly, as shown in the depicted embodiment, each indicator opening 152 has a generally circular shape, with a diameter that is at least slightly larger than the largest diameter of the corresponding seal indicator projection 115.

Further, it will be appreciated that the seal indicator 114 is formed from a deformable material. As described herein, the gasket portion 110 of the combination gasket/filter 122 is compressible and, when the lid 104 is secured to the body 102, the gasket portion 110 is compressed between the lid 104 and body 102 of the container 100 to form a seal between the lid 104 and body 102. In embodiments like the exemplary embodiment in which the seal indicator 114 is formed as part of the gasket portion 110, the seal indicator 114 is formed from the same deformable, compressible material as the gasket portion 110 of the gasket/filter 122. To make the projections 115 formed from such material be invertible, the seal indicator 114 comprises a base 154 at each projection 115. The base 154 of each projection 115 surrounds a proximal end 156 of the projection 115, which is joined to or integrally formed with the base 154. In the depicted embodiment, the proximal end 156 of each projection 115 comprises the smallest diameter of the generally conical projection 115, and the base 154 is generally circular. The gasket portion 110 is generally rounded about each base 154, forming a rounded transition area from a body of the gasket 110 to the base 154 of the seal indicator projection 115.

As shown in FIGS. 10-12, the base 154 of each projection 115 has a thickness $t_{base}$ that is less than a thickness $t_{gasket}$ of the remainder of the deformable material of the gasket portion 110 from which the seal indicator 114 is formed. In some embodiments, the thickness $t_{base}$ of the base 154 is from about 30% to about 70% of the thickness $t_{gasket}$ of the gasket portion 110. In other embodiments, the thickness $t_{base}$ of the base 154 is from about 40% to about 60% of the thickness $t_{gasket}$ of the gasket portion 110. In an exemplary embodiment, the thickness $t_{base}$ of the base 154 is approximately 50% of the thickness $t_{gasket}$ of the gasket portion 110. For example, in terms of a measurement of the thicknesses, in some embodiments the thickness $t_{gasket}$ of the gasket portion 110 is within a range from about 4 mm to about 10 mm, while the thickness $t_{base}$ of the base 154 is within a range from about 2 mm to about 5 mm.

The reduced or decreased thickness $t_{base}$ of the base 154 enables the inversion of each projection 115 when the lid 104 is received on the gasket portion 110. That is, the compression force applied by the lid 104 pushes the projections 115 downward as the lid 104 is lowered onto the projections 115 and gasket portion 110, which is supported by the inner lip 124 of the body 102. The reduced or decreased thickness $t_{base}$ of the base 154 of each projection 115, which extends around the periphery of the proximal end 156 of the projection 115, allows a distal end 158 of the projection 115, as the projection 115 is pushed downward by the lid 104, to pass the base 154 and through the corresponding indicator opening 152 and to continue downward until the distal end 158 is below the base 154 and the projection 115 is inverted from its first, upward position (FIGS. 10, 11) to its second, downward position (FIG. 12). As previously described, the seal indicator 114—namely, the projections 115—is not visible from the container exterior 116 when in its first indicator state, where the projections 115 are in their first, upward position, but is visible from the container exterior 116 when in its second indicator state, where the projections 115 are in their second, downward position and extend through the indicator openings 152 in the inner lip 124 of the container body 102.

Thus, the seal indicator 114 includes features for providing visual indication that a seal is established between the container lid 104 and body 102 that do not require a relatively high compression force or a relatively low durometer material. Rather, the reduced or decreased thickness $t_{base}$ of the base 154 of each projection 115 allows the projections 115 to be inverted without the application of a relatively high compression force by the lid 104. It will be understood that the force applied by the lid 104 activates or deploys the seal indicator 114 such that the indicator 114 indicates to a user when the container 100 is sealed due to the compression of the gasket 110 by the lid 104. Moreover, because of the reduced or decreased thickness $t_{base}$ of the base 154 of each projection 115, the gasket portion 110 of the combination gasket/filter 122, from which the seal indicator 114 is formed, does not have to be a relatively low durometer material to allow the projections 115 to be inverted from their first, upward position to their second, downward position. As an example, the gasket portion 110 may be formed from a material having a durometer or Shore Hardness within a range of about 20 to about 70 on the Shore 00 scale. Further, because the seal indicator 114 is formed as part of the gasket portion 110, the gasket/filter 122 can be formed without any openings therein. More specifically, no openings for a seal indicator or the like need be formed in the gasket portion 110; any openings in the gasket portion 110 could weaken its ability to form a complete seal between the container lid 104 and body 102 and could be a potential pathway for contaminants to enter the container interior 106. Further, any openings in the gasket 110 could shorten the pathway that contaminants must traverse to enter the interior 106; foregoing such openings in the embodiments described herein allows a lengthier pathway because of an increased contact area between the gasket 110 and lid 104 and gasket 110 and inner lip 124, which creates a more tortuous path for contaminants to the interior 106. Thus, it is preferable to form a gasket without any openings therein. Still further, as described herein, at least a portion of each projection 115, such as the distal end 158, may have a color or hue that contrasts with the color of the exterior of one or more other components of the container 100, such as the body 102 and lid 104. The contrasting color can make it easier for a user to ascertain whether the projections 115 extend through the indicator openings 152 to the exterior 116 of the container 110, i.e., whether the container 100 is sealed. For at least the foregoing reasons, the present subject matter provides a seal indicator 114 that is relatively simple or easy to activate or deploy (e.g., because a relatively high or large compression force is not required to push the projections 115 through the indicator openings 152) and is robust (e.g., because use of a very low durometer material can be avoided; no openings need be formed in the gasket portion 110, allowing a wider gasket 110 and/or more contact area between the gasket 110 and lid 104 and gasket 110 and inner lip 124; color on at least a portion of the projections 115 helps allow ease of checking whether the container 100 is sealed).

Accordingly, the sterilization container 100 provides visualization of its seal, i.e., a visual indication that a seal is established between the body 102 and lid 104 sufficient to block contaminants from entering the container 100. Further, such visualization provides an indication of the seal integrity of the container's seal, i.e., whether the seal remains unbroken or uncompromised after the seal is established. As described herein, the seal visualization provided by the seal indicator 114, which protrudes through the indicator openings 152, is binary in nature. That is, the seal indicator 114 transitions from a first state, where the indicator 114 is unseen and the container 100 is open or unsealed, to a second state, where the indicator 114 is seen and the container 100 is closed or sealed. The transition from the first indicator state to the second indicator state may be highlighted with the use of a color or hue on the seal indicator 114 to contrast with, e.g., the body 102 of the container 100.

Referring now to FIGS. 13 through 15, in some embodiments, the sterilization container 100 may include a second lid or cover that fits over at least a portion of the lid 104, e.g., to prevent intrusions through the vent openings 118 defined in the top of the lid 104. For example, it will be appreciated that contaminants or other debris matter could fall through the vent openings 118 illustrated in the exemplary embodiments of the present subject matter, and such contaminants could fall into the container 100 via a compromised filter media 120 or when the container 100 is opened, thus compromising the sterility of the articles within the container 100. As a particular example, an instrument end or the like could enter the vent openings 118, e.g., if the instrument is dropped on the lid 114, and thereby pierce, puncture, cut, tear, etc. the filter media 120 that is positioned between the vent openings 118 and the container interior 106, which could compromise the integrity of the filter media 120 and thereby could compromise the sterility of the articles within the container 100. Therefore, a second lid or cover 160, which also may be referred to as a safety lid or cover 160, may be provided to shield the vent openings 118 defined in the lid 104.

In the exemplary embodiments illustrated herein, the lid 104 includes a raised portion 162 in which the vents or vent openings 118 are defined. As shown in FIG. 13, in an exemplary embodiment of the safety cover 160, the safety cover 160 is configured to fit over the raised portion 162 of the lid 104. Thus, the safety cover 160 does not hinder or interfere with receipt of the lid 104 on the inner lip 124 of the body 102, such that the lid 104 is recessed within the body 102 as described herein. As further depicted in FIG. 13, the safety cover 160 covers the vent openings 118 such that the vent openings 118 are not directly exposed to the external environment. Accordingly, the safety cover 160 may itself have define openings 164 therein for fluids, such as the sterilant of the selected sterilization modality, to enter and exit the container 100. The defined openings 164 of the safety cover 160 are judiciously shaped and sized to ensure the desired Volume to Vent (V-to-V) ratio is maintained. It will be appreciated that such openings 164 may be defined in the safety cover 160 such that the openings 164 do not face the same breach potential as the vent openings 118 in the underlying lid 104. For instance, as shown in FIGS. 13-15, the openings 164 in the safety cover 160 do not align with the vent openings 118 defined in the lid 104, i.e., the openings 164 defined in a top or outer surface 166 of the safety cover 160 are offset from the vent openings 118 when the safety cover 160 is attached to the lid 104. Further, a plurality of openings 164 also are defined along one or more side surfaces 170 of the safety cover 160. In addition to or as an alternative to the openings 164, a gap G (FIG. 15) may be defined between the safety cover 160 and the underlying lid 104, e.g., around the perimeter of the raised portion 162 of the lid 104, such that fluids may enter and exit the container 100 via the gap G between the safety cover 160 and the lid 104.

The safety cover 160 may be releasably attached to the lid 104 or may be durably attached to the lid 104. In the depicted exemplary embodiment, the safety cover 160 is releasably attached to the lid 104 using tabs 168 and posts 172, which pass into the lid 104 to secure the safety cover 160 to the lid. More particularly, two tabs 168 on one side of the safety cover 160 hook in to apertures in the lid 104. On the opposite side of the safety cover 160, two posts 172 protrude from an underside or inner surface 174 of the safety cover 160. Each post 172 passes through a vent opening 118 in the top surface 105 of the lid. Of course, other numbers of tabs 168 and posts 172 may be used as well.

Referring particularly to FIG. 15, the posts 172 are captured by a securing mechanism 176, which is incorporated into the lid 104, to secure the safety cover 160 to the container 100. The safety cover 160 is released by pressing or otherwise manipulating a control member 178, such as a slidable button, which is connected to the securing mechanism 176. The securing mechanism 176 may be, e.g., a spring force mechanism that utilizes the force provided by a spring to capture, hold, and release the posts 172. As shown, e.g., in FIGS. 13 and 15, the lid 104 comprises two halves, an upper half 104a and a lower half 104b, which each define vent openings 118 therein to allow fluid to pass through the lid 104, and the securing mechanism 176 is contained between the two halves of the lid 104. After pressing the button 178, the safety cover 160 would be free, e.g., to allow a user to remove the safety cover 160 for cleaning or other purposes. In embodiments in which the safety cover 160 is durably attached to the lid 104, it may be impossible or highly inconvenient to remove the safety cover 160, which may be undesirable with respect to cleaning the sterilization container 100.

As further shown in FIGS. 13-15, the safety cover 160 defines a handle opening 180 therein for each handle 138 of the sterilization container 100. Thus, in the exemplary embodiment, the safety cover 160 defines two generally circular handle openings 180 for the two generally circular handles 138 of the lid 104. As such, the handles 138 remain operable when the safety cover 160 is attached to the lid 104, e.g., a user can still grasp the first portion 138a of each handle 138 to rotate the handles 138 and engage the cam 142 with the arms 140 such that the arms 140 move to secure or unsecure the lid 104 with respect to the body 102. The handle openings 180 may have any suitable size or shape for handles 138 to protrude through such that the handles 138 are operable when the safety cover 160 is installed on the lid 104.

It will be appreciated that the embodiment illustrated in FIGS. 13-15 is provided by way of example only. The safety cover 160 may have other configurations than as shown in the figures. Further, in some embodiments of the sterilization container 100, a protective lid or cover like safety cover 160 may be unnecessary or undesirable and, thus, may be omitted.

The present subject matter also provides methods for sealing a sterilization container and methods for indicating the integrity of a gasket of a sterilization container. For example, an exemplary method for sealing a sterilization container comprises providing a container body and a container lid that together define an interior for receipt of articles for sterilization. The container body has an open top portion and an inner lip, and the container lid, which rests on the inner lip such that an inside edge of the lid is not exposed to the external environment, covers the open top portion to close the sterilization container. The container lid also comprises a closure mechanism that includes at least one rotatable handle in operative communication with at least two arms. The method further comprises providing a gasket that extends between the container body and the container lid when the container lid is positioned on the container body to seal the interior against an ingress of contaminants. An exemplary container body 102, lid 104, closure mechanism 136, and gasket 110, which is part of a combination gasket/filter 122, are described with respect to the sterilization container 100 discussed herein.

Moreover, the method comprises rotating the at least one rotatable handle to engage the arms with the container body. As described herein, a cam 142 may be disposed between an exemplary rotatable handle 138 and the at least two arms 140. When the handle 138 is rotated, the cam translates the rotating motion of the handle 138 to linear motion of the arms 140. The arms 140 slide through openings in the lid 104, in which the closure mechanism 136 is disposed, and through corresponding rim openings 148 in a rim 128 of the container body 102. By extending through the body 102, the arms 140 prevent the lid 104 from being removed from the body 102. Further, engaging the arms 140 with the body 102 applies force to the gasket portion 110 of the combination gasket/filter 122, compressing the gasket portion 110 between the lid 104 and body 102 and thereby establishing the seal between the body 102 and lid 104. The method also may comprise rotating the at least one rotatable handle to disengage the arms from the container body. For instance, the arms may be disengaged from the body after the sterilization container has undergone a sterilization process to sterilize the contents of the container. As described herein, because the lid is supported on the inner lip, the inside edge of the lid remains separated from the environment external to the container, thereby preserving its sterility post-sterilization. As such, after the arms of the closure mechanism are disengaged from the body and the lid is removed from the body, the inside edge of the lid may be aseptically presented.

As another example, an exemplary method for indicating the integrity of a gasket of a sterilization container comprises providing a container body and a container lid that together define an interior for receipt of articles for sterilization. The container body has an open top portion and an inner lip, and the container lid, which rests on the inner lip such that an inside edge of the lid is not exposed to the external environment, covers the open top portion to close the sterilization container. The method also comprises providing a gasket that extends between the container body and the container lid when the container lid is positioned on the container body to seal the interior against an ingress of contaminants. An exemplary container body 102, lid 104, and gasket 110, which is part of a combination gasket/filter 122, are described with respect to the sterilization container 100 discussed herein.

Further, the method comprises providing a seal indicator for indicating a seal state of the sterilization container. In a first indicator state, the seal indicator is unseen or not visible to a user of the sterilization container, thereby indicating the container is unsealed. In a second indicator state, the seal indicator is seen or visible to the user, thereby indicating the container is sealed against the ingress of contaminants. An exemplary seal indicator 114, which includes projections 115 that protrude through indicator openings 152 in the inner lip 124 of the exemplary container body 102, is described with respect to the sterilization container 100. Additionally, modifications or extensions of the exemplary method for indicating seal integrity also may be realized from the sterilization container embodiments and other subject matter discussed herein.

Also, it will be understood that one or more tags, such as tamper evidence tags and/or contents labels, may be included with each sterilization container. For example, a single use tamper evident tag, which breaks upon opening, may be attached to each sterilization container when the container is sealed. In one embodiment, a tamper evident tag includes a plastic flap across the interface between the container body and lid that tears upon opening. Additionally or alternatively, other tags or labels may be included with each sterilization container described herein. For instance, each container may include a label that, e.g., specifies the contents of the container, the date and time of sterilization, and/or other pertinent information, or a way to access such information, such as a radio-frequency identification (RFID)

tag, a barcode, a matrix or two-dimensional barcode (or Quick Response (QR) code), or other appropriate means for accessing such information.

Accordingly, the present subject matter provides several benefits and advantages over know rigid sterilization containers. For instance, the present subject matter provides a rigid sterilization container with an inside or internal sealing surface, i.e., the inner lip 124 described herein, which is a kind of shelf edge within the body of the container that receives and interacts with a combination gasket/filter. The lid of the sterilization container is designed to fit inside the body and sit on an upper surface of the gasket portion of the combination gasket/filter, which is disposed on the inner lip of the body. The gasket portion of the gasket/filter is compressible by a closing force and interacts with the inner lip to form a mating point or interface between the lid and body of the container. As described herein with respect to an exemplary embodiment, the closure force is provided by a closing mechanism integrated into the lid that is designed to provide at least to two points of force, but preferably four points and more preferably six points of force, to the gasket portion of the gasket/filter. The greater number of points of force improves the distribution of the closing force along the gasket portion and allows more uniform sealing. Thus, particularly in embodiments in which the closure mechanism provides at least four points of force along the gasket portion of the gasket/filter, an even closure force along the four sides of the rigid sterilization container may be provided, which helps ensure uniform sealing of the container interior against contamination.

Further, a seal indicator may be provided that allows for visualization of the container seal when the lid is in place and the closure mechanism is engaged. Such visualization of the seal provides an indication of the seal integrity of the container. As described herein, the seal indicator is binary in nature, going from a first, unseen state, which indicates to a user that the container is open or unsealed, to a second, seen state, which indicates to the user that the container is closed or sealed against contamination of the container interior. The visualization provided by the seal indicator may be highlighted with the use of color or hue as described herein. Therefore, the present subject matter provides a seal indicator for a sterilization container so that the end-user of the container may have confidence the container is uniformly sealed and that the seal has been maintained throughout and post-sterilization. The seal indicator may incorporate features such as a reduced or decreased thickness base that allows activation or deployment of the seal indicator with less or a lower compression force than known seal indicators and allows greater flexibility in choosing an appropriate durometer material than other designs. Further, the seal indicator may be formed as part of a gasket or a combination gasket/filter, which reduces the number of parts in the container assembly. A reduced number of parts may provide advantages such as reduced manufacturing costs and complexity, reduced assembly time, and reduced opportunities for contamination such as bacteria to enter the container interior.

Yet another advantage or benefit of the present subject matter is that the inside edge of the lid is closed, sealed, and not exposed to the outer surface of the sterilization container. Thus, the inside edge of the lid is not exposed to the external environment after sterilization and should be considered free of potential microbial containments associated with the environment. Hence, the inside edge of the lid can be aseptically presented when the lid is opened and removed from the body of the container. Further, providing the sealing interface between the container body and lid at the inside or interior of the sterilization container (i.e., along an inner lip or shelf) reduces the opportunity for damage to the gasket and the sealing surfaces of the lid and body (i.e., the surfaces of the lid and body that contact the gasket). As such, providing the seal between the lid and body along the inner lip or shelf of the body protects the seal, e.g., during transportation of the container, and helps keep the seal secured during handling and storage of the container. Of course, other benefits and advantages also may be realized from the present subject matter.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A sterilization container, comprising:
   a body including a first end, a second end opposite the first end, a first side extending between the first and second ends, and a second side opposite the first side and extending between the first and second ends, the body further including an open top portion;
   a lid for securing to the body to close the open top portion of the body, the body and lid together defining an interior;
   a gasket for sealing the interior against an ingress of contaminants; and
   a seal indicator for indicating a seal state of the sterilization container, the seal indicator comprising an invertible projection, the projection extending in a first direction in a first indicator state, the projection extending in a second direction in a second indicator state, the first direction corresponding to a first position and the second direction corresponding to a second position, the projection invertible from the first position to the second position,
   wherein the first indicator state indicates an unsealed state of the sterilization container and the second indicator state indicates a sealed state of the sterilization container,
   wherein the projection of the seal indicator is visible from an exterior of the sterilization container through an opening in the body when in the second indicator state.

2. The sterilization container of claim 1, wherein the seal indicator is in the first indicator state when the lid is not secured to the body and the gasket is not compressed to seal the sterilization container against the ingress of contaminants, the projection in its first position in the first indicator state such that the seal indicator is not visible from an exterior of the sterilization container, and
   wherein the seal indicator is in the second indicator state when the lid is secured to the body and the gasket is compressed to seal the sterilization container against the ingress of contaminants, the projection in its second position in the second indicator state such that the seal indicator is visible from an exterior of the sterilization container.

3. The sterilization container of claim 1, wherein the projection is in its first position in the first indicator state such that the seal indicator is not visible from an exterior of the sterilization container, and
wherein the projection is in its second position in the second indicator state such that the seal indicator is visible from an exterior of the sterilization container.

4. The sterilization container of claim 1, wherein the projection has a generally conical shape.

5. The sterilization container of claim 1, wherein the seal indicator is formed from a deformable material.

6. The sterilization container of claim 5, wherein the seal indicator comprises a base that surrounds a proximal end of the projection, the proximal end joined to the base, and
wherein the base has a thickness that is less than the thickness of the remainder of the deformable material.

7. The sterilization container of claim 1, wherein the opening has a shape complementary to a cross-sectional shape of the projection.

8. The sterilization container of claim 1, wherein the projection comprises a color that contrasts with a color of the lid and a color of the body.

9. The sterilization container of claim 1, further comprising:
a filter extending across the open top portion of the body from the first end to the second end and from the first side to the second side,
wherein the gasket and filter are integrally formed as a single piece gasket/filter.

10. The sterilization container of claim 1, wherein the body defines an inner lip around an inner surface of the body within the interior of the container, the inner lip recessed inward within the body.

11. The sterilization container of claim 10, wherein the gasket is disposed on the inner lip, and
wherein the lid is supported by the inner lip such that the lid is recessed within the body.

12. The sterilization container of claim 11, wherein the lid has a closure mechanism that includes at least one rotatable handle and at least two arms, the at least two arms configured to protrude through the lid and the body to secure the lid to the body, the handle in operative communication with the at least two arms such that the at least two arms move linearly when the handle is rotated.

13. The sterilization container of claim 12, wherein a rim of the body extends around the inner lip and has a height h over the inner lip, and
wherein at least two rim openings are defined in the rim, each rim opening configured for receipt of a distal end of a respective one of the at least two arms.

14. The sterilization container of claim 12, further comprising:
a safety cover that fits over a raised portion of the lid,
wherein the safety cover defines a plurality of openings or a gap between the safety cover and the lid to allow a fluid to pass from an exterior of the container to the interior, and
wherein the safety cover defines a handle opening therein for the at least one rotatable handle.

15. A sterilization container, comprising:
a body including a first end, a second end opposite the first end, a first side extending between the first and second ends, and a second side opposite the first side and extending between the first and second ends, the body further including an open top portion;
a lid for securing to the body to close the open top portion of the body, the body and lid together defining an interior;
a gasket/filter including a gasket portion for sealing the interior against an ingress of contaminants and a filter portion extending across the open top portion of the body from the first end to the second end and from the first side to the second side, the gasket portion and the filter portion integrally formed as a single piece component; and
a seal indicator for indicating a seal state of the sterilization container, the seal indicator comprising an invertible projection, the projection extending in a first direction in a first indicator state, the projection extending in a second direction in a second indicator state, the first direction corresponding to a first position and the second direction corresponding to a second position, the projection invertible from the first position to the second position,
wherein the first indicator state indicates an unsealed state of the sterilization container and the second indicator state indicates a sealed state of the sterilization container, and
wherein the seal indicator is formed in the gasket portion of the gasket/filter.

16. The sterilization container of claim 15, wherein the lid has a closure mechanism that includes at least one rotatable handle and at least four arms, the at least four arms configured to protrude through the lid and the body to secure the lid to the body, the handle in operative communication with the at least four arms such that the at least four arms move linearly when the handle is rotated.

* * * * *